United States Patent [19]

Barascut et al.

[11] Patent Number: 5,639,873

[45] Date of Patent: Jun. 17, 1997

[54] OLIGOTHIONUCLEOTIDES

[75] Inventors: Jean-Louis Barascut, Combaillaux; Jean-Louis Imbach, Montpellier, both of France

[73] Assignee: Centre National de la Recherche Scientifique (CNRS), Paris, France

[21] Appl. No.: 284,484

[22] PCT Filed: Feb. 4, 1993

[86] PCT No.: PCT/FR93/00115

§ 371 Date: Aug. 4, 1994

§ 102(e) Date: Aug. 4, 1994

[87] PCT Pub. No.: WO93/16095

PCT Pub. Date: Oct. 19, 1993

[30] Foreign Application Priority Data

Feb. 5, 1992 [FR] France ................................. 92 01275
Sep. 17, 1992 [FR] France ................................. 92 11103

[51] Int. Cl.⁶ ............................ C07H 21/00; C07H 21/02; C07H 21/04; C12Q 1/68
[52] U.S. Cl. ........................ 536/25.3; 536/23.1; 536/24.3; 536/24.5; 536/25.31; 536/25.34; 435/6; 435/91.1
[58] Field of Search ................................. 435/6, 91.1, 22.1; 536/23.1, 24.1, 24.3, 24.31, 24.5, 25.3, 25.31, 25.33, 25.34; 514/44

[56] References Cited

U.S. PATENT DOCUMENTS 4,968,602  11/1990  Dattagupta ................................. 435/6

FOREIGN PATENT DOCUMENTS

| 0117777 | 1/1984 | European Pat. Off. . |
| 0169787 | 7/1985 | European Pat. Off. . |
| 2540122 | 1/1983 | France . |
| 2568254 | 7/1984 | France . |
| 2636633 | 9/1988 | France . |
| WO83/01451 | 4/1983 | WIPO . |
| WO88/04301 | 12/1987 | WIPO . |

OTHER PUBLICATIONS

Alderfer et al. "Hydrogen and Carbon NMR Studies on the Conformation of Nucleic Acids Containing 4'–Thio–Furanose", Biophys. J. 25:223a Feb. 1979.

Goodchild "Conjugates of Oligonucleotides and Modified Oligonucleotides..." Bioconjugate Chem. 1:165–187. May 1990.

Anisuzzaman, A. et al., "4'–Thioadenosine 3', 5'–Cyclic Phosphate and Derivatives. Chemical Synthesis and Hydrolysis by Phosphodiesterase", Biochemistry 1973, 12(11), 2041–2045.

Hoffman, D. and Whistler, "Synthesis and Properties of Nucleotides Contianing 4–Thio–D–ribofuranose", Biochemistry 1970, 9(11), 2367–2372.

Primary Examiner—John L. LeGuyader
Assistant Examiner—Thomas G. Larson
Attorney, Agent, or Firm—Woodcock Washburn Kurtz Mackiewicz & Norris

[57] ABSTRACT

Chemical compounds consisting of an alpha or beta oligo-4'-thioribonucleotide or oligo-4'-thio-2'-deoxyribonucleotide characterized in that they comprise a concatenation of 4'-thioribonucleotides or 4'-thio-2'deoxyribonucleotides, respectively. The concatenation is optionally linked to an effector, in particular a radical corresponding to an intercalating agent or a photoactivatable or chemical radical, e.g. a radical carrying a function which reacts directly or indirectly with the nucleotide chains, or a radical whose presence enables easy and sensitive detection. Methods for preparing said compounds, and their uses in therapeutics, diagnostics and as laboratory reagents, are also described.

18 Claims, 1 Drawing Sheet

OLIGOTHIONUCLEOTIDES

FIELD OF THE INVENTION

The present invention relates to new chemical compounds as well as their applications. The chemical compounds according to the present invention are oligonucleotide compounds at least partially consisting of an oligo-4'-thioribonucleotide or an oligo-4'-thio-2'-deoxyribonucleotide comprising a concatenation of 4'-thionucleotides.

BACKGROUND OF THE INVENTION

In French Patent Applications FR 8,301,223 (2,540,122) and FR 8,411,795 (2,568,254) have been described chemical compounds consisting of an oligonucleotide or an oligodeoxynucleotide comprising a concatentation of natural or modified nucleotides, that is to say beta-nucleotides, onto which is attached by a covalent bond at least one intercalating group, which possess the property of selectively blocking the expression of a gene and which, because of this, are particularly useful in therapy as antiviral, antibiotic, antiparasitic or antitumor substances.

In International Application PCT WO 83/01451, has been described a method for blocking the translation of messenger RNA (mRNA) into protein by hybridization of the mRNA with an oligonucleotide having the sequence complementary to the mRNA, the oligonucleotide being stabilized in phosphotriester form.

In International Application WO 88/04301 have been described oligonucleotides of alpha anomeric configuration having parallel pairings with complementary sequences.

Chemotherapy with antisense oligonucleotides relates to RNA or DNA targets of all living organisms (cells, bacteria, parasites, viruses or oncogenes).

The use of synthetic antisense oligonucleotides having the same structure as the natural nucleic acids is faced, mainly in biological medium, with problems of sensitivity to nucleases and cell penetration.

To overcome these limitations, oligonucleotide analogs capable of being more resistant to nucleases and of penetrating better into the cells across the cyto-plasmic membrane have been synthesized.

There has indeed been described in the prior art derivatives of oligonucleotide compounds resisting enzymatic degradations better, whose phosphate part was modified into thiophosphate or methyl phosphonate especially. However, these derivatives exhibit a chirality at the level of the phosphate capable of generating insoluble diastereoisomers.

SUMMARY OF THE INVENTION

The compounds according to the invention may have the natural anomeric configuration beta or the non-natural anomeric configuration alpha.

Thus, alpha(a) and beta(b) 4'-thionucleotides are represented by the formulae(a) and (b) respectively

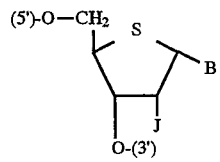

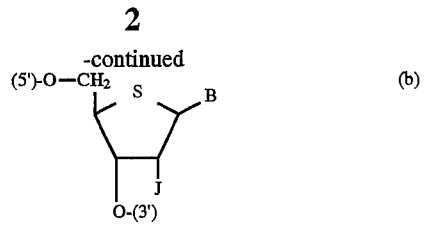

(a) and (b) represent 4'-thionucleosides, a phosphate should be added in 5' in order to obtain nucleotides.

Under these conditions, many uses for biological and even pharmacological purposes already known for oligonucleotides can be envisaged, and this with greater efficiency.

More precisely, the subject of the present invention is chemical compounds consisting of an oligo-4'-thioribonucleotide or an oligo-4'-thio-2'-deoxyribonucleotide, characterized in that they comprise a concatenation of 4'-thioribonucleotides or 4'-thio-2'-deoxyribonucleotides respectively, it being possible for said concatenation to be optionally linked to an effector, especially a radical corresponding to an intercalating agent or a chemical or photoactivable radical, such as a radical carrying a functional group which reacts directly or indirectly with the nucleotide chains or a radical whose presence permits easy and sensitive detection.

In particular, the subject of the invention is new oligo-4'-thionucleotide derivatives, their preparation and their use especially as probes permitting the detection of a defined sequence of nucleic acids, as artificial nucleases specific for DNA or RNA sequences or alternatively as agents for selectively blocking the expression of a gene, whether endogenous (for example oncogene gene) or exogenous (for example DNA or RNA of viruses, parasites or bacteria).

DESCRIPTION OF THE PREFERRED EMBODIMENTS

Figure 1:
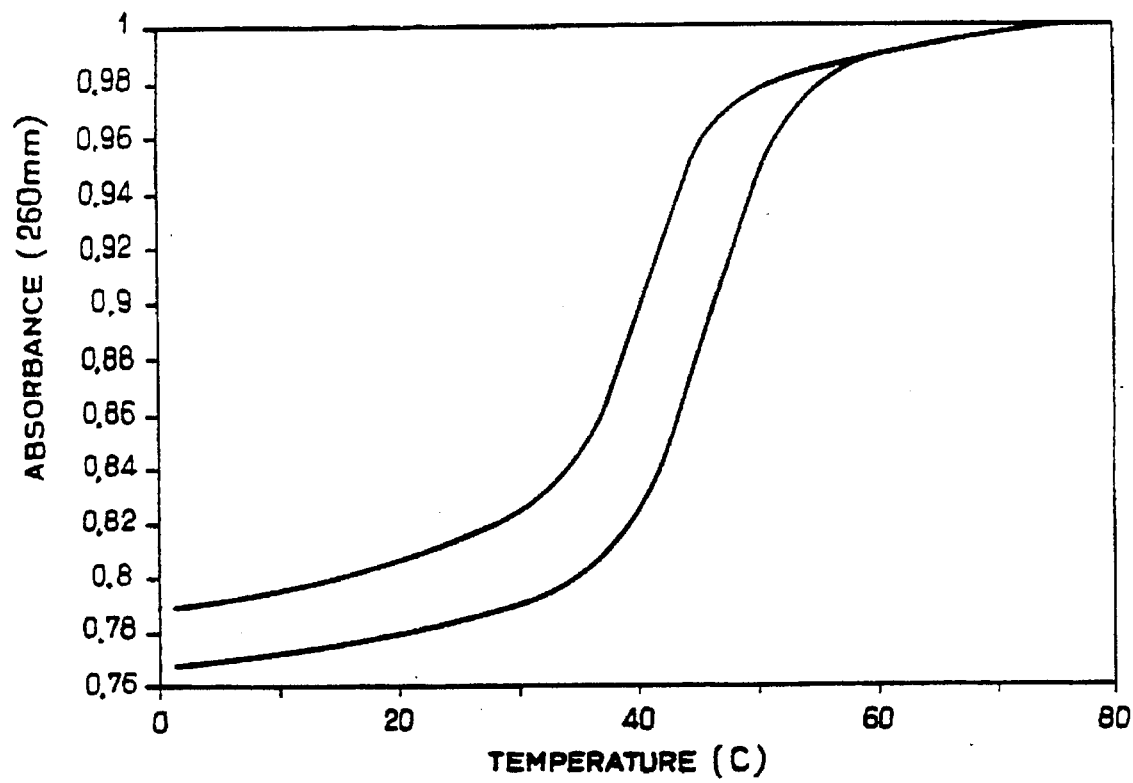
FIG. 1 represents the curve for thermal stability of the betadT$_5$(S$_r$T)dT$_e$(SEQ ID NO: 3)/betadC$_2$A$_{12}$C$_2$(SEQ ID NO: 4) duplex compared with that of the natural betadT$_{12}$ (SEQ ID NO: 3)/betadC$_2$A$_{12}$C$_2$(SEQ ID NO: 4) duplex.

The present invention provides a new class of chimeric oligonucleotides, the 4'-thiooligonucleotides, in which the intracyclic oxygen of the furanose ring has been replaced by a sulfur atom.

It has indeed now been found, and this is what constitutes the subject of the present invention, that the substitution of oxygen by a sulfur on the sugar part of the nucleosides rather than on the phosphate group, on the one hand, ensures the solubility of the oligomers and, on the other hand, could increase their penetration into the target cell, the substitution of oxygen by the sulfur element rendering the molecule more lipophilic.

The derivatives of 4'-thionucleotides form hybridization complexes with the sequences complementary to RNA which are much more stable than those formed with DNA and that, with respect to RNAs, the derivatives of 4'-thionucleotides form hybridization complexes which are more stable than the derivatives of natural beta-nucleotides.

Among the compounds, according to the present invention, there may be mentioned more particularly the beta oligomeric compounds of formula

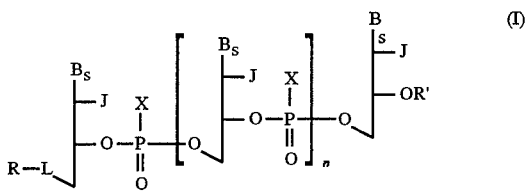

in which the B radicals may be identical or different and each represent a base of a nucleic acid optionally modified, activable and/or comprising an intercalating group;

the X radicals may be identical or different and each represent an oxoanion O⁻, a thioanion S⁻, an alkyl group, an alkoxy or aryloxy group, an aminoalkyl group, an aminoalkoxy group, a thioalkyl group, an alkyl or alkoxy radical substituted by a nitrogen-containing heterocycle or a —Y—Z group;

R and R', which may be identical or different, each represent a hydrogen atom or a —Y—Z or Y'—Z' group;

Y and Y', which are identical or different, each represent a straight or branched alkylene radical —alk— or a radical chosen from

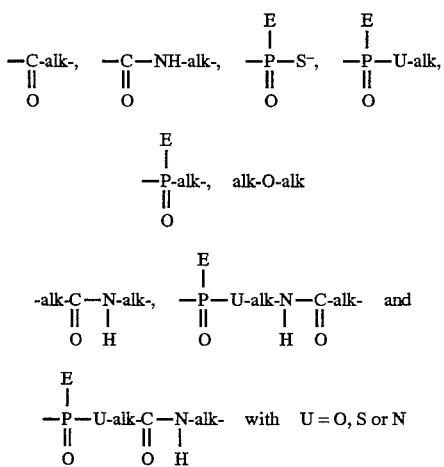

In particular, Y and Y' represent a radical chosen from

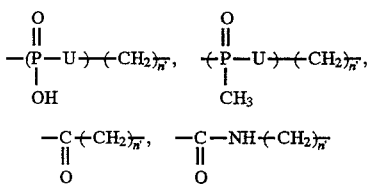

with U=O, S or N

E may have the same meanings as X except Y—Z or Y'—Z';

L represents O, S or —NH—;

n and n' represent an integer including 0;

J represents a hydrogen atom or an hydroxyl group;

Z and Z', which are identical or different, each represent OH or a radical corresponding to an effector, especially a radical corresponding to an intercalating agent or a radical carrying a functional group which reacts directly or indirectly with the nucleotide chains or a radical whose presence permits easy and sensitive detection.

In this formula I, the following condensed representation of nucleotides is used:

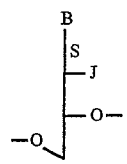

which corresponds to the structural formula:

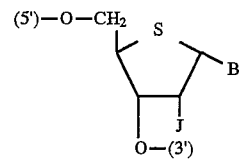

in which the (3') and (5') ends have been stated.

It should be noted that the formula I represents a concatenation of 4'-thionucleotides which may be identical or different, of D or L configuration, n simply indicating the number of nucleotides included in the molecule; n is preferably a number between 1 and 50, and still more preferably between 1 and 25.

There may be mentioned in particular the products for which L represents oxygen; R and R' represent hydrogen and B a natural nucleic base, either adenine, thymine, cytosine or guanine when J=H and adenine, uracil, cytosine and guanine when J=OH.

The intercalating agents are products known in the techniques relating to nucleic acids; they are compounds capable of "becoming intercalated" in the structure of DNAs or RNAs, that is to say capable of becoming inserted between the base plates of nucleic acids.

The intercalating agents may be chosen from the polycyclic compounds having a planar configuration such as acridine and its derivatives, furocoumarin and its derivatives, daunomycin and the other derivatives of anthracycline, 1,10-phenanthroline, phenanthridine and its derivatives, proflavine, porphyrins, derivatives of dipyrido[1,2-a:3',2'-d] imidazole, ellipticine or ellipticinium and their derivatives and diazapyrene and its derivatives.

The reactive chemical radicals may be radicals which can react directly or indirectly with a nucleotide chain to form a covalent bond or in order to modify it chemically, or in order to cut it. Preferably, these reactive chemical radicals are activable, for example, chemically, biochemically or photochemically.

The activable reactive radicals may be chosen from ethylenediaminetetraacetic acid, diethylenetriaminepentaacetic acid, porphyrins, 1,10-phenanthroline, 4-azidoacetophenone, ethylene-imine, beta-chloroethylamine, psoralen and their derivatives, and the aromatic compounds absorbing near-ultraviolet or visible radiations or which can react chemically with the nucleic constituents.

More particularly, the radicals which are chemically activable in the presence of metal ions, oxygen and a reducing agent (ethylenediaminetetraacetic acid, diethylenetriaminepentaacetic acid, porphyrin, phenanthroline) induce the cutting in nucleic acid sequences situated in their vicinity.

By irradiation in the visible or near-ultraviolet region, it is possible to activate the derivatives which absorb these radiations and to carry out bridging reactions or photoinduced reactions (cutting and modification of the nucleic bases) of the nucleic acids on which is attached the oligothionucleotide carrying the activable group.

Among the Z and Z' radicals, there may be mentioned more particularly:

the radicals derived from ethylenediaminetetraacetic acid of formula:

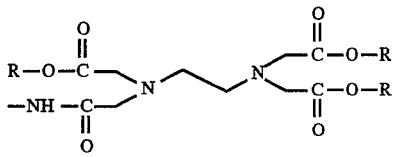

the radicals derived from diethylenetriaminepentaacetic acid, the radicals derived from methylpyrroporphyrin of formula:

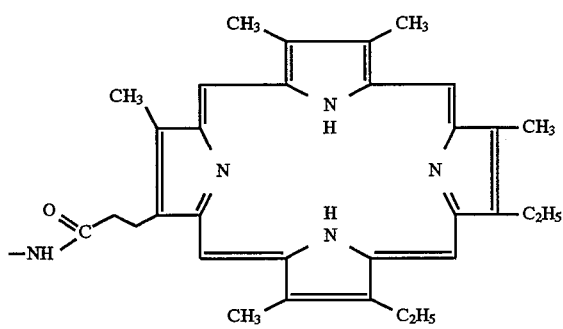

the radicals derived from phenanthroline of formula:

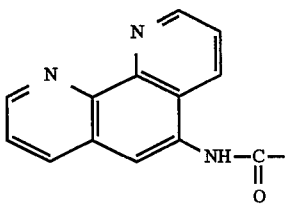

the radicals derived from acridine:

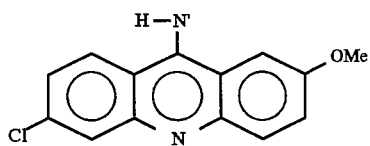

the radicals derived from proflavine

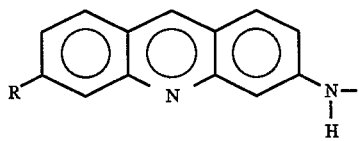

R representing an amino ($NH_2$) or azido ($N_3$) group the radicals derived from biotin

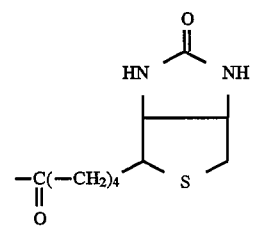

the radicals derived from 4-azidoacetophenone of formula:

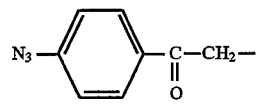

The B radical may be preferably chosen from the natural nucleic bases (thymine, adenins, cytosine, guanine, uracil) but it is possible to use modified nucleic bases. There may be mentioned 2-amino adenine and its derivatives substituted for example on the nitrogen atom $N^6$ by an aminoalkylene radical or by an azidophenylalkylene radical, guanine substituted on the oxygen atom $O^6$ for example by a (w-alkylene)-9-acridine group, (w-aminoalkyl)amino-8-adenine and its derivatives substituted on the amino radical in w by an acridine group, or the halogenated or azide-containing derivatives such as 5-bromo uracil, 8-azidoadenine, 7-deazaadenine and 7-deazaguanine. It is also possible to use derivatives of nucleic bases comprising an intercalating group or a chemically or photochemically activable group.

Thus, the functionalization of C or T by an aziridine group in position 4 leads to the formation of $CH_2$-$CH_2$ covalent bridges between the two complementary strands on G and A respectively. Therefore, more particularly, the B radical is then chosen from 4-azidocytosine or 4-azidothymine.

Preferably, the X radical represents an oxoanion. However, the X radical may represent an alkyl radical containing 1 to 7 carbon atoms (methyl, ethyl, propyl), an alkoxy radical whose alkyl part contains 1 to 7 carbon atoms (methoxy, ethoxy, 2,2-dimethylpropyloxy), an aminoalkyl or aminoalkoxy radical of general formula $R_1R_2N$—alk—A— in which A represents a bond or an oxygen atom, —alk— represents an alkylene radical containing 1 to 10 carbon atoms and $R_1$ and $R_2$, which are identical or different, represent a hydrogen atom or an alkyl radical containing 1 to 7 carbon atoms or form, together with the nitrogen atom to which they are bonded, a 5- or 6-membered saturated nitrogen-containing heterocycle, it being understood that the $R_1R_2N$-group may be quaternized, or an alkylthio radical whose alkyl part contains 1 to 7 carbon atoms.

In the formula (I), the —alk— radical is preferably a straight or branched alkylene radical having 1 to 10 carbon atoms.

In particular, from the 3' or 5' terminal alcohol functional groups of the oligothionucleotide, the effector Z can therefore by introduced via a chain $(CH_2)_n$ linked to a functionalization Z', of diverse natures, to the glycoside part of the oligomer.

From the following formula:

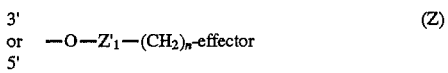

there will be obtained, depending on what $Z'_1$ represents, for example
a phosphate or methyl phosphonate of formula

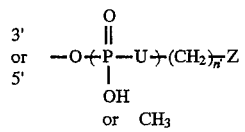

$U=O$, $N$ or $S$
an ether of general formula

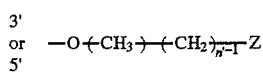

an ester of general formula:

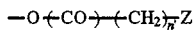

or alternatively
a carbamate of general formula:

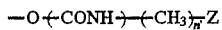

In general, n' is between 1 and 10.

The present invention also relates to the preceding compounds in the form of a salt with bases or acids, and the compounds in racemic form, in the form of R or S optical isomers, purified or in a mixture, of formula (I).

The present invention preferably relates to the preceding compounds of formula (I) in the D series.

There may be mentioned in particular the D-oligothionucleotide compound products of general formula:

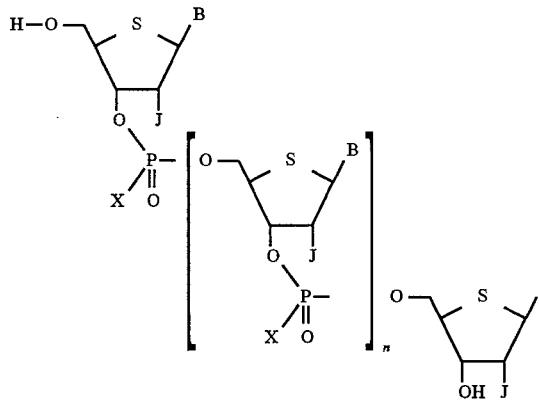

in which J and X are defined as above for the compounds of formula (I) and B represents a natural nucleic base.

The oligonucleotides according to the present invention may exist in the form of homogeneous sequences, as in the compounds of formula (I) or in the form of mixed oligomers, that is to say in the form of specific sequences included in other types of DNA or RNA type oligonucleotides, modified or otherwise, at the level of the phosphate concatenation, the latter corresponding to compounds of formula (I), in which the intracyclic oxygen of the furanose ring is restored.

The subject of the present invention is therefore also mixed oligomeric compounds characterized in that they consist of oligothionucleotide compounds according to the invention linked to DNA or RNA type oligonucleotides. By "DNA or RNA type oligonucleotides" there is understood here a sequence of DNA or RNA type nucleic acids modified or otherwise at the level of the phosphate concatenation and in which the intracyclic heteroatom of the furanose ring of the nucleotides is oxygen.

The subject of the present invention is especially mixed oligomeric compounds consisting of an oligothionucleotide sequence according to the invention, comprising a DNA or RNA type oligonucleotide sequence within it or at one of its ends.

In a specific embodiment, therefore, the oligonucleotide sequence, of the DNA or RNA type, is flanked by two oligothioribonucleotide sequences.

The new products of general formula (I) or mixed oligomers containing them can be prepared chemically by known processes and, in particular, those which are described in known process applications and, in particular, those which are described in French Patent Applications FR 8,310,223 (2,540,122) and FR 8,441,795 (2,568,254), WO 88/04301 and FR 88 122648.

The oligothionucleotide compounds especially of formula (I) can be prepared chemically by processes in which conventional phosphodiester, phosphotriester, phosphoramidite or hydrogen phosphonate syntheses are applied for oligonucleotides.

In these processes, the 4'-thionucleotide chain is first prepared, the various groups not used being protected, and then the protecting groups are finally removed in order to obtain the desired products.

There may be mentioned in particular a process for the synthesis of oligothionucleotide compounds according to the invention without effector, characterized in that a supported synthesis is carried out according to the phosphoroamidite method comprising a protection in 3' and 5' of the starting 4'-thionucleotides or oligo-4'-thionucleotides with for example dimethoxytrityl in 5' and methyl diisopropylaminophosphoramidite in 3', the functionalization of a solid support incorporating a 4'-thionucleoside derivative by for example a succinyl linkage between the 3'-hydroxyl group of the 4'-thionucleoside derivative and an amino group of the solid support, the elongation of the oligothionucleotide chain in a synthesizing reactor, finally the detachment, deprotection and purification of the extended oligothionucleotide.

There may also be mentioned a process for the synthesis of oligothionucleotide compounds incorporating an effector according to the invention, characterized in that there is used as starting material an oligothionucleotide without effector, or a mixed oligomer containing it, protected in 5', whose 3' OH end is reacted with an unprotected functional group of a difunctional arm whose second functional group is protected and after deprotection of the resulting product, said product is linked to the effector by the second free functional group of the difunctional arm.

The 3' OH end of the oligomer protected in 5' can be esterified with an aminohexanoic acid, whose amine functional group is protected.

A process for the solid phase preparation of oligothionucleotide sequences according to the phoshoramidite method, which is the subject of the present invention, comprises the following essential steps:

A 4'-thionucleoside derivative, protected by means of one of its hydroxyl functional groups in 3' or, where appropriate, 2', is immobilized on a solid support.

The protected oligothionucleotide chain is assembled on this support, in a manual or automatic synthesizing reactor, by condensation of monomers consisting of protected 4'-thionucleosides substituted by phosphoramidite groups in 3', where appropriate, the hydroxyl functional group in 2' of the riboses being protected by Ctmp or TBDMS groups.

The oligothionucleotides are obtained after detachment of the oligomer obtained from the support and removal of the protecting groups.

Appropriately, the assembling of the oligothionucleotide is carried out by condensation, in the presence of an activating agent, of said monomers between their 3' functional group and the 5' functional group of the immobilized 4'-thionucleoside compound for the first monomer or of an intermediate protected polythionucleotide compound attached to said immobilized thionucleoside compound for the following monomers.

In particular, the activating agent for the condensation of said monomers may be chosen from tetrazole and its derivatives, such as para-nitrophenyltetrazole.

Advantageously, the phosphoramidite group in 3' of said monomers is an N,N-dialkylaminophosphoramidite group of formula

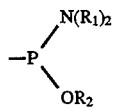

with $R_1$, which represents an optionally substituted $C_1$ to $C_7$ alkyl, which may be identical or different, such as $CH_3$ or $(CH_3)_2CH$.

$R_2$ which represents an optionally substituted $C_1$ to $C_7$ alkyl, such as $CH_3$ or $CH_2CH_2CN$.

In particular, the phosphoramidite group in 3' of said monomers is methyl diisopropylaminophosphoramidite ($R_1=(CH_3)_2CH$ and $R_2=CH_3$) or 2-cyanoethyl diisopropylaminophosphite ($R_1=(CH_3)_2CH$ and $R_2=CH_2CH_2CN$).

Appropriately, the hydroxyl groups of said monomers and of said immobilized 4'-thionucleoside compound may be protected in 5' by the DmTr group.

The immobilized 4'-thionucleoside compound may be attached to the solid support via a divalent succinyl group between one of its OH groups in 2' or 3' which thus becomes esterified, and an amino group of the support.

The solid support may consist of a long alkyl-amine chain attached to a polymer, a silica gel or porous glass beads.

There may be mentioned as functional group permitting the attachment or being linked to a solid support provided with an amino group, the group of formula

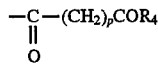

with p=1 to 5, in which $R_4$ represents H, an activating group such as $C_6Cl_5$ or a radical NH linked to a solid support such as the NH radical of an alkylamine chain attached to a polymer, silica gel or porous glass beads.

One virtue of the homogeneous or mixed compounds according to the present invention, comprising an oligothionucleotide chain, is that it is possible to envisage their use independently of effectors, especially intercalating agents, since these new oligonucleotide substances ensure the recognition of the complementary nucleic acid sequence, especially RNA sequence, with a highly increased stability; the function of the intercalating agent being to increase the stability of the hybridization complex, its presence is no longer obligatory.

The compounds according to the invention, by virtue of their high oligothionucleotide sequence-specific affinity for complementary nucleic sequences, are indeed superior to the current oligonucleotides whose affinity for the complementary sequences is lower.

The compounds according to the present invention can therefore be used more efficiently, as hybridization probes, but also as purification components for given DNA or RNA sequences.

These compounds can also be used to detect mutations at the level of a DNA or an RNA more efficiently.

The compounds of the present invention, by virtue of the property of the oligothionucleotide sequences to become strongly attached to the complementary nucleic sequence, and then to induce the cutting of the nucleic acid chain at this site, especially when they are coupled to a cutting agent, can be used as sequence-specific artificial nucleases. They can be used as reagents in molecular biology and in genetic engineering.

The presence of the hydroxyl functional group in 2', where appropriate, makes it possible, in addition, to envisage their use as artificial ribozymes, whether in the form of oligothioribonucleotide sequences which are homogeneous or mixed, that is to say associated with DNA or RNA type oligonucleotides.

The subject of the present invention is also the application of the compounds according to the invention to carry out the specific blocking of cellular genes or of pathogenic agents chosen beforehand (viruses, bacteria, parasites).

The compounds according to the invention can therefore also be used as medicinal products.

The new products of general formula (I) according to the invention and the products of general formula (I) in which L represents an oxygen atom, R and R' each represent a hydrogen atom and B represents a natural nucleic base, form hybridization complexes with the complementary RNA sequences which are much more stable than those which are formed with DNA.

In particular, the products of formula (I) in which J=OH (oligothioribonucleotides) pair more stably with complementary RNA sequences than the products of formula (I) in which J=H (oligothiodeoxyribonucleotides).

Given the fact that the targets for the antisense molecules in therapy are the messenger RNA genes, this property of oligothioribonucleotides is quite useful.

This difference in the stability of the hybridization complexes permits a preferential inhibition of the messenger RNAs and viral RNAs with no great risk of causing undesirable effects at the level of the DNA of the genome.

Furthermore, with respect to the RNAs, the products according to the invention generally form complexes which are more stable than those which are obtained from natural oligonucleotides.

The oligothioribonucleotide compounds according to the invention, especially of formula (I) (J=OH), exhibit, in addition, a number of useful characteristics, especially for an application as antisense agents:

the natural beta configuration is preserved, they are isoelectric with the natural RNAs, they have no chirality at the level of the phospho-diester bond, they are more lipophilic than the natural analogs because of the presence of the sulfur atom.

The sequences of the oligothionucleotides, coupled or not to an intercalating agent or to a chemically or photochemically activable group, comprising a concatenation of pyrimidine nucleosides are capable of attaching to a DNA or RNA double helix comprising a sequence of adjacent purine bases associated by hydrogen bond with the complementary sequence of the pyrimidine bases. This attachment involves the local formation of a triple helix in which the pyrimidine bases of the oligothionucleotide form hydrogen bonds (Hoogsteen or reversed Hoogsteen type) with the purine bases of the double helix. In this context, the oligothionucleotides form complexes which are more stable than the corresponding oligonucleotides and they make it possible to induce irreversible reactions (bridging, modification or cutting) on an RNA or DNA double helix.

The new products of general formula (I) according to the invention and the products of general formula (I) in which L represents an oxygen atom, R and R' each represent a hydrogen atom and B represents a natural nucleic base, which possess the property of attaching strongly to the complementary nucelic sequence, or mixed oligomers containing it, can be used as probes to detect the presence of a complementary nucleotide chain. This detection is facilitated by the presence of a fluorescent group or a biotin group in these molecules.

The non-natural structure of the oligothionucleotides confers properties of antigenicity thus rendering possible the preparation of specific antibodies directed against oligothionucleotides optionally coupled to an intercalating agent or against their complexes with a natural DNA or RNA.

For diagnostic or prognostic purposes, the oligothionucleotides, optionally coupled to an intercalating agent, or mixed oligomers containing them, can be covalently attached to a solid support. The coupling to a luminescent marker or a marker generating a colored, luminescent or fluorescent reaction makes it possible to use them as probes for DNA or RNA sequences for diagnostic or prognostic purposes.

The oligothionucleotides according to the invention are much more resistant to nucleases than the natural nucleoside derivatives. This stability with respect to enzymatic hydrolysis permits the use of the products according to the invention, especially of general formula (I), or mixed oligomers containing them, in experimentations in vivo or in vitro in the presence of nucleases. Because of this, the oligothionucleotides according to the invention have unquestionable advantages over the beta-nucleoside derivatives already mentioned.

The oligothioribonucleotide compounds of formula (I) for which J=OH are more resistant to enzymatic degradation than the oligothiodeoxyribonucleotide compounds of formula I for which J=H.

Consequently, as has been seen, another subject of the present invention relates to the application of the new products according to the inventionk especially of general formula (I), and of the products of general formula (I) in which L represents an oxygen atom, R and R' each represent a hydrogen atom and B represents a natural nucleic base, in particular the products for which J=OH, or mixed oligomers containing them, to the specific blocking of cellular genes or pathogenic agents chosen beforehand (viruses, bacteria, parasites), in particular mRNAs.

The new products according to the invention, especially of general formula (I), and the products of general formula (I) in which L represents an oxygen atom, R and R' each represent a hydrogen atom and B represents a natural nucleic base, in particular the products for which J=OH, or mixed oligomers containing them, are particularly useful as medicinal products which make it possible to block the undesirable exogenous.(viruses, bacteria, parasites) or endogenous (cellular genes, oncogenes) genes, in particular the mRNAs. The expression of these genes may be blocked by acting either directly on the DNA or RNA carrying the genetic information, or on the messenger RNA, a copy of the gene, by blocking, in this case, any translation by hybridization or by hybridization followed by bridging or modification or cutting of the messenger or viral RNA chosen as target.

This blocking can be carried out using a product according to the invention, especially of general formula (I), or a product of general formula (I) in which L represents an oxygen atom, R and R' each represent a hydrogen atom and B represents a natural nucleic base, in particular the products for which J=OH, or mixed oligomers containing them, whose sequence is complementary to that of a non-complexed region of an RNA or a DNA and, in particular, of a messenger RNA. The hybridization, followed or not by bridging, modification or cutting of the messenger or vital RNA, prevents the synthesis of RNA or of the corresponding protein or the expression of the viral or parasitic functions.

If this RNA or this protein is vital for the virus, the bacterium or the parasite, the products according to the invention, especially of general formula (I), and the products of general formula (I) in which L represents an oxygen atom, R and R' each represent a hydrogen atom and B represents a natural nucleic base, in particular the products for which J=OH, or mixed oligomers containing them, will constitute medicinal products with antiviral, antibacterial or antiparasitic activity.

If this RNA or this protein is not vital to the organism, it is possible to selectively suppress the effects therefrom. In this case, the products according to the invention, especially of general formula (I), and the products of general formula (I) in which L represents an oxygen atom, R and R' each represent a hydrogen atom and B represents a natural nucleic base, in particular the products for which J=OH, or mixed oligomers containing them, will constitute either medicinal products with antitumor activity when the desired gene or its messenger RNA encodes a protein involved in cell transformation, or medicinal products capable of suppressing the character of resistance to antiviral agents, to antibiotics or to antiparasitic agents when the protein encoded is responsible for the inactivation of the antibiotics, the antiviral agents or the anti-parasitic agents.

Specific cytotoxic effects can be obtained by action of a product according to the invention, especially of formula (I), or of a product of general formula (I) in which L represents an oxygen atom, R and R' each represent a hydrogen atom and B represents a natural base, in particular the products for which J=OH, or mixed oligomers containing them, on a cellular function essential to the target cell.

The mixed oligomers of oligothioribonucleotides according to the invention, comprising an oligonucleotide sequence of DNA where the intracyclic oxygen is restored, are particularly valuable when used as antisense agents. These mixed oligomers are capable of being highly selective insofar as the "window" of DNA structure is the only substrate of RNAse H after pairing of the antisense with its target complementary mRNA sequence, the said RNAse H inducing, in this case, the cutting of the DNA/RNA complex.

Other characteristics and advantages of the present invention will appear in the light of the following examples.

In the following description, the abbreviation rS or $S_r$ precedes a thioribonucleotide.

I-SYNTHESIS OF THIONUCLEOTIDES

I.1- The First Syntheses of Thiosugars Were Carried Out Between 1960 and 1970

Two examples are given:

The synthesis of derivatives of 4-thio-D-ribo-furanose is carried out according to scheme 1:

B. URBAS and R. L. WHISTLER, *J. Org Chem.*, 1966, 31, 813–816.

E. J. REIST, D. E. GUEFFROY and L. GOODMAN, *J. Am. Chem. Soc.*, 1964, 86, 5658–5663.

R. L. WHISTLER and J. N. BeMILLER in "*Methods in Carbohydrate Chemistry*", R. L. WHISTLER and M. L. WOLFROM, Eds., Academic Press, Inc., New York, 1962. Vol. I, p. 79.

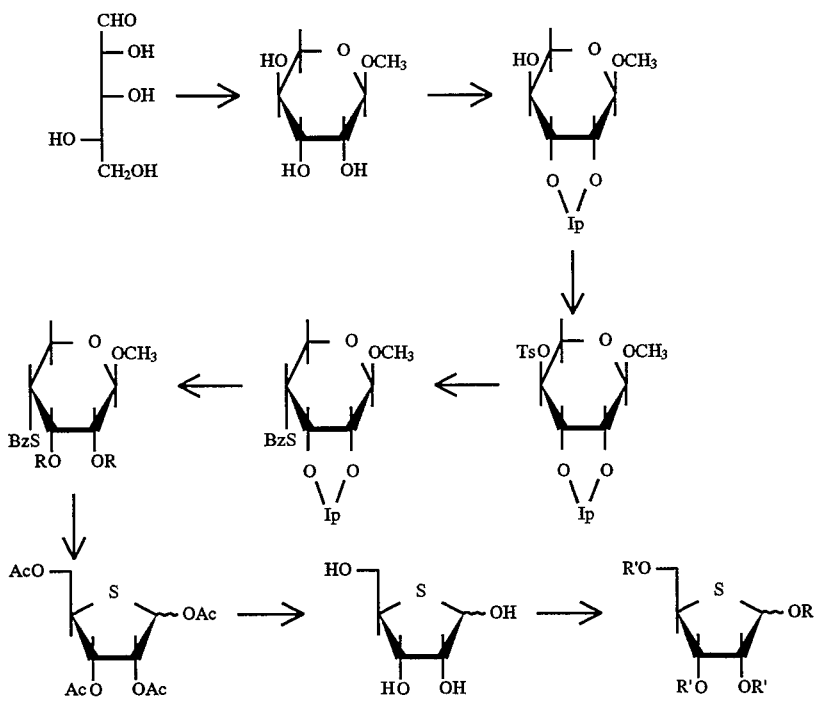

SCHEME 1

This compound is obtained in 8 steps from L-Lyxose with an overall yield of 6%.

R. L. WHISTLER, W. E. DICK, T. R. INGLE, R. M. ROWELL and B. URBAS. *J. Org. Chem.*, 1964, 29, 3723–3725.

The derivatives of 4-thio-2-deoxy-D-ribofuranose were obtained according to Scheme 2:

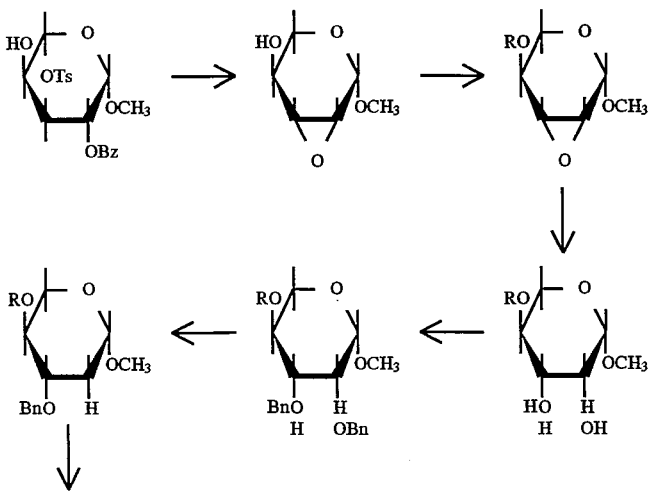

SCHEME 2

-continued
SCHEME 2

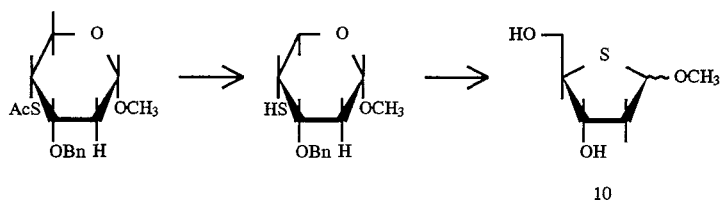

This synthesis in 14 steps leads to methyl 2-deoxy-4-thio-D-erythro-pentofuranoside with an overall yield of 8%.

Y. L. FU and M. BOBEK, *J. Org. Chem.* 1976, 41, 3831–3834

Y. L. FU and M. BOBEK, in *"Nucleic Acid Chemistry"*, L. TOWSEN and R. S. TIPSON, Eds. 1978, Part 1 pp. 183–194

U. G. NAYAK and R. L. WHISTLER *Liebigs Ann. Chem.*, 1970, 741, 131–138

Similarly, the derivatives of 4-thio-D-arabinofuranose were obtained

R. L. WHISTLER, U. G. NAYAK and W. PERKIN Jr., *J. Org., Chem.*, 1970, 35, 519–521

I.2. The corresponding nucleosides were then synthesized:

a) In 4'-thio-2'-deoxy-D-ribofuranose series

Y. L. FU and M. BOBEK in *"Nucleic Acid Chemistry"*, L. TOWSEND, R. L. TIPSON, Eds., John Wiley & Sons, New York, 1978, p. 317.

b) In 4'-thio-D-ribofuranose series

E. J. REIST, D. E. GUEFFROY and L. GOODMAN, *J. Am. Chem. Soc.*, 1964, 86, 5658–5663.

E. J. REIST, D. E. GUEFFROY and L. GOODMAN, *Chem. Ind.*, 1964, 1364–1365

B. URBAS and R. L. WHISTLER, *J. Org. Chem.*, 1966, 31, 814–816

M. BOBEK, R. L. WHISTLER and A. BLOCH. *J. Med. Chem.*, 1970, 13, 411–413

M. BOBEK, A. BLOCH, R. PARTHASARATHY and R. L. WHISTLER, *J. Med. Chem.*, 1975, 18, 784–787.

M. BOBEK, R. L. WHISTLER and A. BLOCH, *J. Med. Chem.*, 1972, 15, 168–171

N. OTOTANI and R. L. WHISTLER, *J. Med. Chem.*, 1974, 17, 535–537

M. W. PICKERING, J. T. WITKOWSKI and R. K. ROBBINS, *J. Med. Chem.*, 1976, 19, 841–842.

A. K. M. ANISUZZAMAN and M. D. AMIN, *J. Bangladesh Acad. Sci.*, 1978, 2, 59–64

D. J. HOFFMAN and R. L. WHISTLER, *Biochemistry*, 1970, 9, 2367–2370 c) In other series:

R. G. S. RITCHIE and W. A. SZAREK, *J. Chem. Soc. Chem. Commun.*, 1973, 686

E. J. REIST, L. V. FISCHER and L. GOODMAN, *J. Org. Chem.*, 1968, 33, 189.

R. L. WHISTLER, L .W. DONER and U. G. NAYAK, *J. Org. Chem.*, 1971, 36, 108.

These nucleosides are obtained by the traditional routes for the synthesis of nucleosides in oxygen-containing series.

Either by the method using heavy metal salts:

Treatment of chloromercuric heterocycle with the corresponding chlorosugar

M. BOBEK, R. L. WHISTLER and A. BLOCH, *J. Med. Chem.*, 1972, 15, 168–171

D. E. GUEFFROY and L. GOODMAN, *Chem. & Ind.*, 1964, 1364–1365

E. J. REIST, M. BOBEK, R. L. WHISTLER and A. BLOCH, *J. Med. Chem.*, 1970, 13, 411–413

E. J. REIST, D. E. GUEFFROY and L. GOODMAN, *J. Am. Chem. Soc.*, 1964, 86, 5658–5663.

E. J. REIST, L. V. FISCHER and L. GOODMAN, *J. Org. Chem.*, 1968, 33, 189–192

Or by the HILBERT and JOHNSON method, by condensation of the pyrimidine base with the corresponding thiochlorosugar B. URBAS and R. L. WHISTLER, *J. Org. Chem.*, 1966, 31, 813–816.

by condensation of the silylated derivatives of the bases and the corresponding thiochlorosugars M. BOBEK, A. BLOCH, R. PARTHASARATHY and R. L. WHISTLER, *J. Med. Chem.*, 1975, 18, 784–787

R. L. WHISTLER, L. W. DONER and U. G. NAYAK, *J. Org. Chem.*, 36, 108–110

N. OTOTANI and R. L. WHISTLER, *J. Med. Chem.*, 1974, 17, 535–537.

By the reaction of fusion of 3-cyano-1,2,4-triazole and 1,2,3,5-tetra-O-acetyl-4-thio-D-ribo-furanose.

M. V. PICKERING, J. T. WITKOWSKI and R. K. ROBINS, *J. Med. Chem.*, 1976, 19, 841–842.

By the VORBRUGGEN and NIEDBALLA method by condensation of adenine and 1,2,3,5-tetra-O-acetyl thioribofuranose in the presence of FRIEDEL-CRAFTS catalyst.

A. K. M. ANISUZZAMAN and M. D. AMIN, *J. Bangladesh Acad. Sci.*, 1978. 2, 59–64

Recently, the synthesis of thionucleosides has again attracted interest

Thus, 2',3',5'-tri-O-benzyl-4'-thio-β-D-xylofuranosyl uracil was obtained by a novel route according to Scheme 3:

M. W. BREDENKAMP, C. W. HOLZAPFEL and A. D. SWANEPOEL, *Tetrahedron Lett.* 1990, 31, 2759–2762.

M. W. BREDENKAMP, C. W. HOLZAPFEL and A. D. SWANEPOEL, *S. Afr. J. Chem.* 1991, 44. 31–33.

SCHEME 3

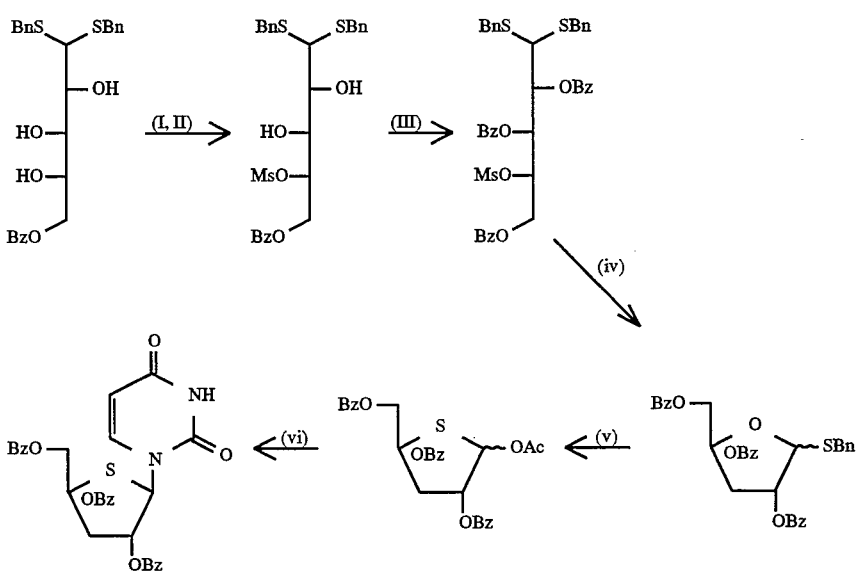

(i = dibutyltin oxide; ii = MsCl; iii = BnCl; iv = tetrabutylammonium iodide, barium carbonate;
v = Hg(OAc)$_2$/AcOH; vi = Modified HILBERT JOHNSON method.)

The synthesis of pyrimidine analogs of 4'-thio-2'-deoxy-nucleosides has been published M. R. DYSON, P. L. COE and R. T. WALKER, *J. Med. Chem.*, 1991, 34, 2782–2786. by the HORTON and MARKOVS method.

D. HORTON and R. A. MARKOVS, *Carbohydrate Res.*, 1980, 80, 356.

It is illustrated by Scheme 4:

SCHEME 4

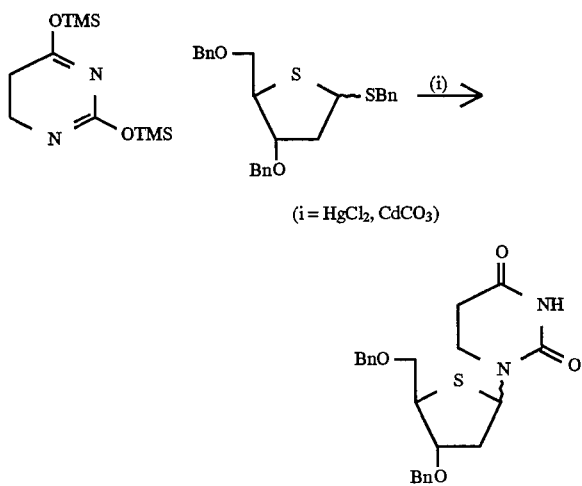

(i = HgCl$_2$, CdCO$_3$)

Similarly, 2'-deoxy-4'-thiocytidine, 2'-deoxy-4'-thiouridine and 4'-thiothymidine were obtained by J. A. SECRIST III et al., (J. A. SECRIST, K. N. TIWARI, J. M. RIORDAN and J. A. MONTGOMERY, *J. Med. Chem.*, 1991, 34, 2361–2366); (J. A. MONTGOMERY and J. A. SECRIST III. PCT Int. Appl. WO 9104,033) from 2-deoxy-4-thio-β-D-erythropentofuranose synthesized according to BOBEK et al., (Y. L. FU, M. BOBEK, *J. Org. Chem.*, 1976, 41, 3831–3834) using TMSTf as coupling catalyst.

The synthesis of 4'-thio-2'-deoxy-D-ribofuranose has been the subject of a patent and publications European Patent Application, 0421 777 A1, R. T. WALKER.

M. R. DYSON, P. O. COE and R. T. WALKER, *J. Chem. Soc. Chem. Comm.*, 1991, 741–742.

M. R. DYSON, P. L. COE and R. T. WALKER, *Carbohydrate Res.*, 1991, 216, 237–248

It is described in Scheme 5:

SCHEME 5

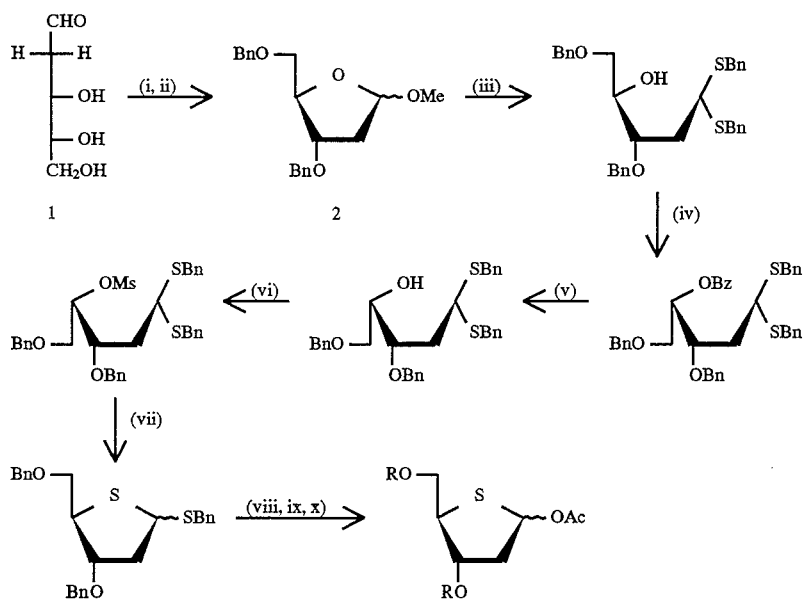

(i = HCl/MeOH, ii = BnBr/THF, iii = BnSH/HCl, iv = Ph₃P/DEAD/BzOH/THF,
v = MeONa/MeOH/CH₂Cl₂, vi = MsCl/Pyr, vii = NaI/CO₃Ba/acetone,
viii = BCl₃/CH₂Cl₂, ix = p-toluoylCl, x = Ac₂O/H₂SO₄)

Ribothionucleosides derived from pyrimidines were the subject of the same patent. But the synthesis of the starting thioribofuranose was carried out according to the method of E. J. REIST.

E. J. REIST, D. E. GUEFFROY and L. GOODMAN, *J. Am. Chem. Soc.*, 1964, 84, 5658

I.3. SYNTHESIS OF SYNTHONS OF 4'-THIO-BETA-D-RIBOFURANOSE NECESSARY FOR THE PRODUCTION OF THIOOLIGOMERS

The synthesis of L-thioLyxofuranose and D-thioRibofuranose was carried out in 7 steps from D-ribose and L-lyxose respectively with 29 and 21% yield respectively. This synthesis is illustrated in Scheme 6.

The synthesis in order to obtain the thio-D-ribofuranose uses L-lyxose as starting product as in the Whistler synthesis (page 19). This strategy is called strategy C1–C4. Indeed, the sulfur atom is first introduced in the anomeric position and an NS2 nucleophilic substitution between the sulfur atom carried by the anomeric carbon (C1) and the C4 carbon carrying an OH activated by a Mesyl (Ms) group is then carried out. This strategy applied to the synthesis of 4-thio-D-ribofuranose and 4-thio-L-lyxofuranose resembles that which Walker used to obtain the 2-deoxy-D-ribofuranose series (Patent Eur. Pat. 0421 777 A 1 page 6). For example, WALKER's product 5 (Scheme 5) is similar to our product 10 (Scheme 6) in L-lyxofuranose series.

SCHEME 6

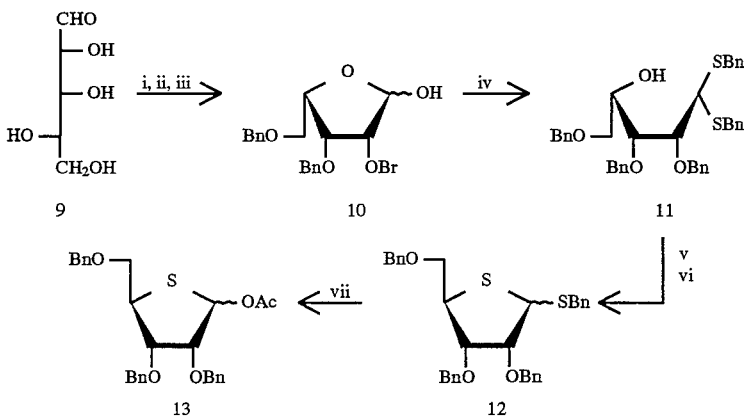

(i = MeOH, HCl; ii = BnBr, KOH; iii = HCL, H₂O, dioxane; iv = BnSH, HCl;
v = MesCL, pyr.; vi = NBu₄I, BaCO₃; vii = Hg(OAc)₂)

SCHEME 7

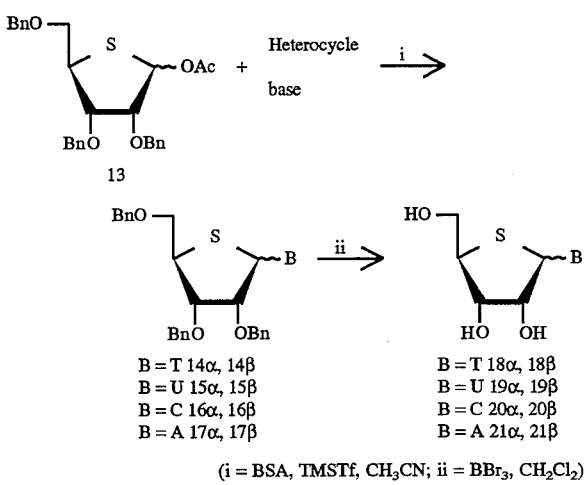

B = T 14α, 14β
B = U 15α, 15β
B = C 16α, 16β
B = A 17α, 17β

B = T 18α, 18β
B = U 19α, 19β
B = C 20α, 20β
B = A 21α, 21β

(i = BSA, TMSTf, CH$_3$CN; ii = BBr$_3$, CH$_2$Cl$_2$)

The synthesis of the thionucleosides of uracil, thymine and cytosine was carried out using bis-trimethylsilyl acetamide (BSA) as silylating agent and trimethylsilyl trifluoromethanesulfonate (TMSTf) as coupling agent. The O and β nucleosides were obtained with 74, 77 and 70% yields respectively. The synthesis of the thionucleosides of adenine was carried out with SnCl4 in acetonitrile. The O and β nucleosides are obtained with 58% yield (Scheme 7).

II. SYNTHESIS OF OLIGOTHIONUCLEOTIDES ON A SOLID SUPPORT

The supported synthesis of β oligothioribonucleotides was carried out with the aid of an APPLIED BIOSYSTEM 318A model GENE synthesizer according to the phosphoramidite method.

It is similar to that described for the natural β oligodeoxyribonucleotide series by CARUTHERS et al., (S. L. BEAUCAGE and M. H. CARUTHERS, Tetradedron Lett., 1981, 22, 1859-1862; L. J. MCBRIDE and M. H. CARUTHERS, Tetrahedron Lett., 1983, 24, 245-248.) and to that described by USMAN et al., for the oligoribonucleotides (N. USMAN, K. K. OGILVIE, M. Y. JIANG and R. J. CEDERGREN, J. Am. Chem. Soc., 1987, 109, 7845-7854.).

This synthesis required:

I) The preparation of synthons β thioribonucleoside phosphoramidites 5 corresponding to the bases T, U, C, A and G.

II) The functionalization of the solid support incorporating a β thioribonucleoside derivative.

III) The elongation of the oligothioribonucleotide chain by means of an automatic synthesizer.

IV) Finally, at the end of the required number of synthesis cycles, the oligothionucleotide was detached from its support, deprotected and purified.

II.1—Synthesis of the Phosphoramidite of the Beta-thioribonucleoside 26 a–d.

II.1.1 Synthesis of 5'-DmTr-2'-O-TBDMS Derivatives (Scheme 8)

The major problem in the chemical synthesis of the oligoribonucleosides is the presence of hydroxyl in 2' in the ribose or thioribose ring which requires a selective protection.

The selection of a protecting group for the hydroxyl in 2' should correspond to several criteria; it should be stable:

under the coupling conditions during the deprotection of the protecting groups in 5' to allow the extension of the chain, during the oxidation in the case of the phosphite triester method, during the masking which follows the coupling, during the deprotection of the exocyclic amine-protecting groups during the deprotection of the phosphates, and in the case of the syntheses on a solid support during the cleavage of the oligomer from the support.

Finally, this protecting group should be removed under very mild conditions to avoid an attack of the liberated hydroxyl functional group in 2' on the adjacent phosphodiester bond.

A large number of strategies for protecting the hydroxyls in 2' have been developed and illustrate the difficulties in the choice of the scheme for protection of the hydroxylated functional groups (C. B. REESE, Nucléosides Nucléotides, 1985, 4, 117–127; R. KIERZECK, M. H. CARUTHERS, C. E. LONGFELLOW, D. SWINTON, D. H. TURNIER and S. M. FREIER, Biochemistry, 1986, 25, 7840–7846; S. IWAI and E. OHTSUKA, Nucleic Acids Res., 1988, 16, 9443–9456; C. LEHMANN, Y. Z. XU, C. CHRISTODOULOU, Z. K. TAN and M. J. GAIT, Nucleic Acids Res. 1989, 17, 2379–2390; T. TANAKA, S. TAMATSUKURI and M. IKEHARA, Nucleic Acids Res.. 1986, 14, 6265–6279.).

The use of alkylsilyl protecting groups and especially tert-butyldimethylsilyl (TBDMS) for the hydroxyl in 2' has facilitated the synthesis of oligoribonucleotides. The TBDMS group is sufficiently stable under acidic or basic conditions and is easily removed by tetra-butyl ammonium fluoride in THF for use in the solid phase strategy (N. USMAN, K. K. OGILVIE, M. Y. JIANG and R. L. LEDERGEN, J. Am. Chem. Soc., 1987, 109, 7845–7854; N. USMAN, K. NICOGHOSIAN, R. L. CEDERGREN and K. K. OGILVIE, Proc. Natl. Sci. USA, 1988, 85, 5764–5768; S. A. SCARINGE, C. F. FRANCKLYN and N. USMAN, Nucleic Acids Res., 1990, 18, 5433–5441; K. K. OGILVIE and M. J. NEMER, Tetrahedron Lett., 1980, 21, 4159; R. T. PON and K. K. OGILVIE, Nucléosides Nucléotides, 1984, 3, 485; R. T. PON and K. K. OGILVIE, Tetrahedron Lett., 1984, 25, 713).

The protection scheme used for the oxygen-containing nucleosides (Scheme 8) was therefore applied in β oligothioribonucleotide series Namely the following protections:

benzoyl for adenine and cytosine, isoButyl for guanine as protection for the exocyclic amino groups, dimethoxytrityl (DmTr) to protect the primary hydroxyls in 5', tert-butyldimethylsilyl (TBDMS) to protect the secondary hydroxyl in 2', methoxy for the protection of the phosphates.

The first step makes it possible to protect the free hydroxyl in 5' by a labils acidic group DmTr (Scheme 8). Thus, the nucleoside derivative 22 is treated with dimethoxytrityl chloride (1.27 molar equivalents) in anhydrous pyridine under an inert atmosphere. After the usual treatment of the reaction mixture, the dimethoxytritylated derivative 23 is purified by silica gel chromatography and isolated with yields ranging from 70 to 80%.

The physico-chemical characteristics of these derivatives 23 (NMR, mass) are in agreement with the proposed structures.

SCHEME 8

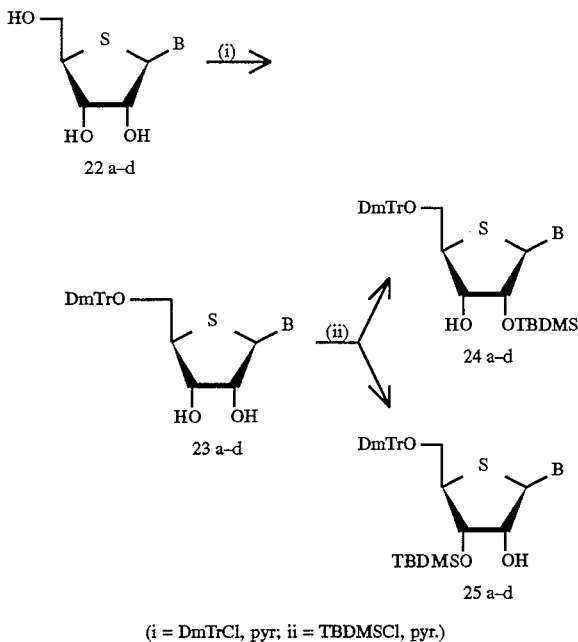

(i = DmTrCl, pyr; ii = TBDMSCl, pyr.)

The abbreviations have the following meanings:
a- B = T = Thymine
b- B = U =Uracile
c- B = CBz = N-Benzoyl-4-Cytosine
d- B = Abz = N-Benzoyl-6-Adenine
e- B = GPal = N-Palmitoyl-2-Guanine
Dmtr = Dimethoxy-4,4'-trityl, iPr = Isopropyl, Bz = Benzoyl, TBDMS = tert-butyldimethylsilyl, (iPr)$_2$P(Cl)OMe = Chloro, (N,N-diisopropylaminomethoxyphonsphine)

The second step (Scheme 8) consists in protecting the secondary hydroxyl in 2'. However, during the silylation, a mixture of 2'-O-silyl 24 and its regioisomer 3'-O-silyl 25 is obtained (K. K. OGILVIE and D. W. ENTWISTLE, Carbohyd. Res., 1981, 89, 203–210, K. K. OGILVIE, A. L. SCHIFMAN and C. L. PENNEY, Can. J. Chem., 1979, 57, 2230, G. H. HAKIMELAHI, Z. A. PROBA and K. K. OGILVIE, Can. J. Chem., 1982, 60, 1106). These isomers should be separated with great care on a silica gel column in order to obtain the 2'-O-TBDMS 24 derivative with a purity greater than 99.95% measured by HPLC. Indeed, if this is not the case, the subsequent steps will lead us to the expected mixtures of 5'-3' oligothionucleotide with the undesirable 5'-2' isomer. Consequently, the purity of the 5'-O-DmTr-2'-O-silyl 24 is of prime importance for a good synthesis.

Thus, the production of the compounds 5'-DmTr-2'-O-TBDMS 24 was first carried out according to the method of OGILVIE et al., (K. K. OGILVIE, A. L. SCHIFMAN and C. L. PENNEY, Can. J. Chem., 1979, 57, 2230) which consists in condensing 23 with tert-butyldimethylsilyl chloride (TBDMSCl) (1.2 molar equivalent) in pyridine in the presence of imidazole (2.6 molar equivalents). At the end of the reaction, a mixture of 2'-O-TBDMS derivative 24 and its 3'-O-TBDMS isomer 25 is obtained. The expected compound 24 is separated from the mixture by chromatography on a silica gel column.

It is then possible, by an equilibration reaction, to obtain 24 from its 3'-O-TBDMS isomer 25 (S. S. JONES and C. B. REESE, J. Chem. Soc. Perkin Trans I, 1979, 2762).

This migration of the TBDMS group is intramolecular and occurs via an intermediate possessing a pentavalent silicon atom. The isomerization of the 3'-O-TBDMS derivative previously obtained after a first chromatographic separation is carried out in ethanol at room temperature overnight. The two position isomers thus obtained are again separated by chromatography on a silica gel column. This isomerization operation followed by a purification is repeated three times.

However, the 5'-DmTr-2'-O-TBDMS 24 yields obtained by this method (40 to 50% according to the bases), did not appear to us to be satisfactory. We used another more recent method developed by OGILVIE (G. H. HAKIMELAHI, Z. A. PROBA and K. K. OGILVIE, Can. J. Chem., 1982, 60, 1106) which permits the preferential introduction of TBDMS in postion 2' of the β ribonucleosides. This technique recommends the use of silver salts.

Thus, 5'-dimethoxytrityl 23 is condensed with TBDMS chloride (1.3 molar equivalents) in the presence of silver nitrate (1.2 molar equivalents) and 3.7 equivalents of pyridine in anhydrous THF. After purification by chromatography on a silica gel column, 56% yield of 24 and 27% of 5'-DmTr-3'-O-TBDMS 25 are obtained. Consequently, 5'-DmTr-2'-O-TBDMS 24 is obtained under these new conditions in a single step with a better yield but the selectivity of introduction of the TBDMS group in 2' is not improved.

II.1.2. Synthesis of the Phosphoramidite
Derivatives 26 a–d (Scheme 9)

The four N-protected β thioribonucleoside phosphoramidites 26 a–d are then obtained from the corresponding N-protected 5'-DmTr-2'-O-TBDMS β thioribonucleosides 24 (Scheme 9).

The nucleoside derivative 24 was treated with chloro-N, N-diisopropylaminomethoxyphosphine (2.5 molar equivalents) in the presence of N,N,N-diisopropylethylamine (DIEA) in dichloromethane under an inert atmosphere. The phosphoramidite derivative 26 was purified by silica gel chromatography and freeze-dried in benzene. The phosphoramidites 26 a–d are obtained with yields ranging from 78 to 80% depending on the nature of the base.

SCHEME 9

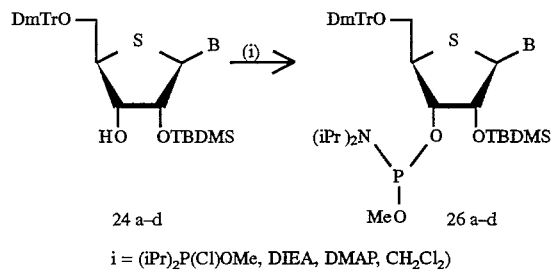

i = (iPr)$_2$P(Cl)OMe, DIEA, DMAP, CH$_2$Cl$_2$)

Analyses of the $^{31}$P and $^1$H NMR spectra of 26 show clearly that a single pair of diastereoisomers is obtained, which establishes the regioisomeric purity of the compounds obtained.

Indeed, some authors (R. KIERZEK, M. H. CARUTHERS, C. E. LONGFELLOW, D. SWINION, D. H. TURNER and S. M. FREIER, Biochemistry, 1986, 25, 7840–7846) had emitted the hypothesis that the silylated groups in position 2' were not stable under the phosphorylation conditions. However, it was shown (W. K. KOHLER, W. SCHLOSSERM, G. CHARUBALA and W. PFLEIDLERER, *Chemistry and Biology of Nucleosides and Nucleotides*, Academic Press, New York, 1978, pp. 347–358; K. K. OGILVIE and D. W. ENTWISTLE, *Carbohydrate Res.*, 1981, 89, 203–210; N. USMAN, K. K. OGILVIE, M. Y. JIANG and R. J. CEDERGREN, *J. Am. Chem. Soc.*, 1987, 109, 7845–7854) that the alkylsilyl groups migrate in protic solvents such as methanol or in aqueous solutions such as a pyridine/water mixture but these silylated groups are stable in anhydrous solvents and especially in non-protic bases such as anhydrous pyridine (K. K. OGILVIE, D. W. ENTWISTLE, *Carbohydrate Res.*, 1981, 89, 203–210; W. KOHLER, W. SCHLOSSER, G. CHARUBALA and W. PFLEIDERER, *Chemistry and Biology of Nucleosides and Nucleotides*, Academic Press, New York, 1978, pp. 347–358). Moreover, it has been clearly demonstrated in ribonucleotide series that the use of the 2'-O-silyl ribonucleosides in the synthesis of oligoribonucleotides lead exclusively to 5'-3' bonds (K. K. OGILVIE, M. J. NEMER, *Tetrahedron Lett.*, 1980, 21, 4159; R. T. PON and K. K. OGILVIE, *Tetrahedron Lett.*, 1984, 25, 713; R. T. PON and K. K. OGILVIE, *Nucleosides Nucleotides*, 1984, 3, 485; P. J. GAREGG, I. LINDH, J. STAWINSKI and R. STOMBERG, *Tetrahedron Lett.*, 1986, 27, 4055–4058). The synthesis of phosphoramidites is not stereospecific and the formation in equal quantities of these two disasteroisomers is due to the chirality of the phosphorus atom of R or S configuration. The formation of these two products is not disruptive insofar as the subsequent oxidation reactions suppress this chirality.

II.2. EXPERIMENTAL PART

General Method for the Preparation of the 5'-O-dimethoxy-trityl-N-acyl-4'-thio-β-D-ribonucleosides 23 a–d.

Dimethoxytrityl chloride (1.27 mmol, 430 mg) is added to a solution of N-acyl-β-D-thioribonucleoside 23 a–d (1 mmol) in anhydrous pyridine (5.6 ml). The reaction mixture is stirred at room temperature under an inert atmosphere for 90 to 120 min and then methanol (1 ml) is added. After stirring for an additional 10 minutes, the reaction mixture is poured over a saturated aqueous sodium bicarbonate solution (25 ml) and the products are extracted with dichloromethane (2×20 ml). The organic phases are washed with water (2×100 ml) and then dried over sodium sulfate and filtered. The filtrate is evaporated under reduced pressure and the residue obtained is chromatographed on a silica gel column. The elution is carried out with a $CH_2Cl_2$/MeOH mixture: 98/2 in the presence of 1% triethylamine; the fractions containing the product are evaporated to dryness and the nucleosides 23 a–d are obtained in the form of an oil.

1-[4'-thio-5'-O-dimethoxytrityl-β-D-ribofuranosyl] Thymine 23 a.

Yield: 68%

Mass spectrometry FAR>0 NOBA m/z=577 [M+H]+, 303 [DmTr]+

$^1$H NMR (DMSOd$_6$, 360 MHz) δ11.24, (s, 1 H, NH); 7.44, (s, 1 H, H$_6$); 6.87–7.30, (m, 13 H, H Aromatic); 5.83, (d, 1 H, H$_{1'}$, J$_{1',2'}$=7.0); 5.53, (d, 1 H, OH$_{2'}$, J$_{OH,2'}$=5.8); 5.30 (d, 1 H, OH$_{3'}$, J$_{OH,3}$=4.7); 4.14 (dd, 1 H H$_{2'}$, J$_{2',1}$=6.9, J$_{2',3}$=3.0); 4.00, (t, 1 H, H$_3$, J$_{3',2}$=3.0, J$_{3',4}$=3.0); 3.69, (s, 6 H, OMe); 3.30, (dd, 1 H, H$_{4'}$); 3.13, (m, 2 H, H$_{5'}$, H$_{5''}$); 1.60, (s, 3 H, CH$_3$).

1-[4'-thio-5'-O-dimethoxytrityl-β-D-ribofuranosyl]Uracil 23 b.

Yield: 70%

$^1$H NMR (DMSOd$_6$, 360 MHz) δ11.31, (s, 1 H, NH); 7.70, (d, 1 H, H$_6$, J$_{6,5}$=8.0), 7.40–6.89, (m, 13 H, aromatic H of the dmTr group ); 5.84, ( d, 1 H, H$_{1'}$, J$_{1',2}$=5.7), 5.53, (d, 1 H, OH$_{2'}$, J$_{OH2',2}$=5.6), 5.48, (d, 1 H, H$_5$, J$_{5,6}$=8.0); 5.26, (d, 1 H, OH$_{3'}$, J$_{OH3',3}$=4.45); 4.02, (m, 2 H, H$_{2'}$, H$_{3'}$); 3.74, (s, 6 H, OMe); 3.31, (m, 3 H, H$_{4'}$, H$_{5'}$, H$_{5''}$)

Mass spectrometry FAB>0 NOBA m/z=563 [M+H]+, 303 [DmTr]+1-[4'-thio-5'-O-dimethoxytrityl-β-D-ribofuranosyl] N-4-benzoylCytosine 23 c.

Yield 69%

$^1$H NMR (DMSOd$_6$, 250 MHz) δ11.32, (s, 1 H, NH); 8.40, (d, 1 H, H$_6$, J$_{6,5}$=7.5); 8.01, (d, 2H, Ho of the benzoyl group); 7.63, (d, 1H, H$_5$, J$_{5,6}$=7.3); 7.44, (m, 17H, aromatic H of the DmTr group and Hm,p of the benzoyl group); 5.88, (d, 1H, H$_{1'}$, J$_{1',2}$=4.1); 5.73 (d, 1H, OH$_{2'}$, J$_{OH,2}$=5.2); 5.27 (d, 1H, OH$_{3'}$, J$_{OH,H3}$=5.7); 4.06 (m, 1H, H$_{2'}$, J$_{2',1}$=4.0, J$_{2',3}$32 3.7, J$_{2',OH}$=5.2); 4.03, (m, 1H, H$_{3'}$, J$_{3',2}$=3.7, J$_{3',4}$=5.3, J$_{3',OH}$=5.7); 3.76, (s, 6H, OCH$_3$ of the DmTr group); 3.43, (m, 3H, H$_{4'}$, H$_{5'}$ and H$_{5''}$).

Mass spectrometry FAB>0 NOBA m/z=666 [M+H]+, 517 [M+HøCONH$_2$]+, 303 [DmTr]+

1-[4'-thio-5'-O-dimethoxytrityl-β-D-ribofuranosyl]N6-benzoylAdenine 23 d.

Yield 70%

$^1$H NMR (DMSOd$_6$, 250 MHz) δ11.25, (s, 1 H, NH); 8.63, (s, 1H, H$_8$); 8.57, (s, 1H, H$_2$); 8.04, (d, 2H, Ho of the benzoyl group); 7.51, (m, 13H, aromatic H of the DmTr group); 6.92, (d, 3H, Hm,p of the benzoyl group); 5.98, (d, 1H, H$_{1'}$, J$_{1',2}$=5.8); 5.75, (d, 1H, OH$_{2'}$, J$_{OH,2}$=3.5); 5.45, (d, 1H, OH$_{3'}$, J$_{OH,3}$=2.5); 4.70, (m, 1H, H$_{2'}$); 4.26, (m, 1H, H$_{3'}$); 3.74, (s, 6H, OCH$_3$ of the DmTr group); 3.53, (m, 3H, H$_{4'}$, H$_{5'}$ and H$_{5''}$)

Mass spectrometry FAB>0 NOBA m/z=690 [M+H]+, 303 [DmTr]+

General method for the preparation of the 2'-O-tert-butyldimethylsilyl-4'-thio-5'-O-dimethoxytrityl-N-acyl-β-D-ribonucleosides 24 a–e and their 3'-TBDMS isomer 25 a–e.

Silver nitrate (1.2 mmol, 203 mg) is added to a solution of 5'-O-dimethoxytrityl-4'- thio-N-acyl-β-D-ribonucleoside 23 a–d (1 mmol) in anhydrous THF (10 ml). The reaction mixture is then stirred for 5 minutes at room temperature before adding tert-butyldimethylsilyl chloride (TBDMSCl, 1.3 mmol, 195 mg) and anhydrous pyridine (3.7 mmol, 0.193 ml). The stirring at room temperature is then continued for 24 h and then the heterogenous solution is filtered before being poured into a 5% aqueous sodium bicarbonate solution (30 ml). The products are extracted with dichloromethane (3×20 ml) and the organic phases are washed with water and then dried over sodium sulfate and filtered. The liltrate is evaporated to dryness and the residue is chromatographed on a silica gel column using as eluent a $CH_2Cl_2$/AcOEt mixture: 95/5 and then with a $CH_2Cl_2$/AcOEt mixture: 80/20. The fractions containing the desired product (2'-O-TBDMS, 24 a–d) are pooled and evaporated to dryness. The 3'-O-TBDMS isomer 25 a–d is then obtained.

1 -[2'-O-tert-butyldimethylsilyl-4'- thio-5'-O-dimethoxytrityl-β-D-ribofuranosyl]Thymine 24 a.

yield: 33%

Mass spectrometry FAB>O NOBA m/z=691 [M+H]+, 713 [M+Na]+

$^1$HNMR (DMSOd$_6$, 300 MHz) δ11.36, (s, 1 H, NH); 7.58, (s, 1H, H$_6$); 7.33–6.90, (m, 13H, aromatic H); 5.89, (s, 1H, H$_{1'}$, J$_{1',2}$=6.1); 5.27, (m, 1H, OH$_{3'}$); 4.20, (dd, 1H, H, H$_{2'}$, J$_{2',1}$=6.10, J$_{2',3}$=3.5); 3.97, (m, 1H, H$_{3'}$); 3.73, (s, 6H, OMe); 3.36, (m, 1H, H$_{4'}$), 3.25, (m, 2H, H$_{5'}$, H$_{5''}$); 1.58, (s, 3H, CH$_3$); 0.81, (s, 9H, tert-butyl); 0.0 (d, 6H, Me$_2$Si).

1-[2'-O- tert-butyldimethylsilyl-4'-thio-5'-O-dimethoxytrityl-β-D-ribofuranosyl]Uracil 24 b.

Yield: 56% m.p.=114° C.

$^1$H NMR (DMSOd$_6$, 360 MHz) δ11.20, (s, 1 H, NH); 7.81, (d, 1H, H$_6$, J$_{6,5}$=8.1); 7.30–6.89, (m, 13H, aromatic H of the dmTr group) 5.84, (d, 1H, H$_{1'}$, J$_{1',2}$=5.5); 5.50, (d, 1H, H$_5$, J$_{5,6}$=8.1); 5.23, (d, 1H, OH$_{3'}$, J$_{OH3',3}$=4.7); 4.11, (q, 1H, H$_{2'}$, J$_{2',1}$=5.5, J$_{2',3}$=3.5); 3.95, (m, 1H, H$_{3'}$); 3.74, (s, 6H, OMe); 3.38, (m, 2H, H$_{4'}$, H$_{5'}$, J$_{4',5}$=3.28, (m, 1H, H$_{5''}$); 0.82, (s, 9H, tert-butyl); 0.05, (m, 6H, Me$_2$Si).

Mass spectrometry FAB>0 NOBA m/z=677 [M+H]+, 619 [M+H-tert-butane]+, 303 [dmTr]+

1-[2'-O-tert-butyldimethylsilyl-4'-thio-5'-O-dimethoxytrityl-β-D-ribofuranosyl]-N4-benzoylCytosine 24 c.

Yield: 32%

$^1$H NMR (DMSOd$_6$, 250 MHz): δ11.31, (s, 1 H, NH); 8.51, (d, 1H, H$_6$, J$_{6,5}$=7.3); 8.01, (d, 2H, Ho of the benzoyl group); 7.51, (m, 14H, aromatic H of the DmTr group and H$_5$); 6.93, (d, 3Hm,p of the benzoyl group); 5.93, (d, 1H, H$_{1'}$, J$_{1',2}$=3.0); 5.20, (d, 1H, OH$_{3'}$, J$_{OH,H3'}$=5.0); 4.14, (m, 1H, H$_{2'}$); 4.00, (m, 1H, H$_{3'}$); 3.76, (s, 6H, OCH$_3$ of the DmTr group); 3.38, (m, 3H, H$_{4'}$, H$_{5'}$ and H$_{5''}$); 0.86, (s, 9H, tert-butyl); 0.60, (d, 6H, Me$_2$Si).

Mass spectrometry FAB>0 NOBA m/z 780 [M+H]$^+$, 303 [DmTr]$^+$

1-[2'-O-tert-butyldimethylsilyl-4'-thio-5'-O-dimethoxytrityl-β-D-ribofuranosyl]-N6-benzoylAdenine 24 d.

Yield: 35%

$^1$H NMR (DMSOd$_6$, 250 MHz): δ11.25, (s, 1 H, NH); 8.64, (s, 1H, H$_8$); 8.61, (s, 1H, H$_2$), 8.04, (d, 2H, Ho of the benzoyl group); 7.51, (m, 13H, aromatic H of the DmTr group); 6.95, (d, 3H, Hm,p of the benzoyl group); 6.01, (d, 1H, H$_{1'}$, J$_{1',2}$=5.8); 5.48, (d, 1H, OH$_{3'}$, J$_{OH,3}$=2.5); 4.70, (m, 1H, H$_{2'}$); 4.26, (m, 1H, H$_{3'}$); 3.75, (s, 6H, OCH$_3$ of DmTr group); 3.53, (m, 3H, H$_{4'}$, H$_{5'}$ and H$_{5''}$); 0.82, (s, 9H, tert-butyl); 0.50, (d, 6H, Me$_2$Si).

Mass spectrometry FAB>0 NOBA m/z=804 [M+H]+, 303 [M+H]+

1-[3'-O-tert-butyldimethylsilyl-4'- thio-5'-O-dimethoxytrityl-β-D-ribofuranosyl]Thymine 25 a.

Yield: 13%

$^1$H NMR (DMSOd$_6$, 360 MHz): δ11.34, (s, 1 H, NH); 7.46, (s, 1H, H$_6$); 7.89–7.30, (m, 13H, aromatic H); 5.87, (d, 1H, H$_{1'}$, J$_{1',2}$=7.8); 5.46, (d, 1H, OH$_{2'}$, J$_{OH,2}$=5.1); 4.13, (m, 1H, H$_{3'}$); 4.11, (m, 1H, H$_{2'}$, J$_{2',1}$=7.8, J$_{OH,2}$=5.1); 3.73, (s, 6H, OMe); 1.66, (s, 3H, CH$_3$); 0.84, (s, 9H, tert-butyl); 0.50, (d, 6H, Me$_2$Si).

1 - [3'-O-tert-butyldimethylsilyl -4'-thio-5'-O-dimethoxytrityl-β-D-ribofuranosyl]Uracil 25 b.

Yield: 27% m.p.=109° C.

$^1$H NMR (DMSO$_6$, 360 MHz): δ11.30, (s, 1 H, NH); 7.70, (d, 1H, H$_6$, J$_{6,5}$=8.0); 7.30–6.89, (13 H, aromatic H of the dmTr group); 5.84, (d, 1 H, H$_{1'}$, J$_{1',2}$=7.3); 5.57, (d, 1 H, H$_5$, J$_{5,6}$=8.0); 5.46, (d, 1 H, OH$_{2'}$, J$_{OH2',2}$=5.1); 4.12, (t, 1 H, H$_{3'}$, J$_{3',2}$=3.1, J$_{3',4}$=3.1); 4.03, (m, 1H, H$_{2'}$); 3.74, (s, 6H, OMe) ;3.41, (m, 1H, H$_{4'}$); 3.21, (m, 2H, H$_{5'}$, H$_{5''}$); 0.08, (s, 9H, tert-butyl); 0.02 (m, 6H, Me$_2$Si).

Mass spectrometry FAB>0 NOBA m/z=677 [M+H]+, 619 [M+H-tert-butane]+, 303 [dmTr]+.

This compound was brought into contact with a 0.25% (v/v) ethanol/triethylamine solution for 12 h at room temperature in order to give, in equal proportions, a mixture of 24 b and 25 b.

1-[3'-O-tert-butyldimethylsilyl-4'-thio-5'-O-dimethoxytrityl-β-D-ribofuranosyl]-N4-benzoylCytosine 25 c.

Yield: 31%

$^1$H NMR (DMSOd$_6$, 250 MHz): δ11.33, (s, 1 H, NH); 8.40, (d, 1H, H$_6$, J$_{6,5}$=7.4); 8.01, (d, 2H, Ho of the benzoyl group); 7.60 (m, 14H, aromatic H of the DmTr group and H$_5$); 6.92, (d, 3H, Hm,p of the benzoyl group); 5.92, (d, 1H, H$_{1'}$, J$_{1',2}$=5.3); 5.60, (d, 1H, OH$_{2'}$, J$_{OH,2}$=5.0); 4.15, (m, 2H, H$_{2'}$, H$_{3'}$); 3.75 (s, 6H, OCH$_3$ of the DmTr group); 3.38, (m, 3H, H$_{4'}$, H$_{5'}$, and H$_{5''}$); 0.79, (s, 9H, tert-butyl); 0.00, (d, 6H, Me$_2$Si)

Mass spectrometry FAB>0 NOBA m/z 780 [M+H]$^+$, 303 [DmTr]$^+$

1-[3'-O- tert-butyldimethylsilyl-4'-thio-5'-O-dimethoxytrityl-β-D-ribofuranosyl]-N6-benzoylAdenine 25 d.

Yield: 29%

$^1$H NMR (DMSOd$_6$, 250 MHz): δ11.25, (s, 1 H, NH); 8.64, (s, 1H, H$_8$); 8.61, (s, 1H, H$_2$); 8.04, (d, 2H, Ho of the benzoyl group); 7.51, (m, 13H, aromatic H of the DmTr group); 6.95, (d, 3H, Hm,p of the benzoyl group); 6.01, (d, 1H, H$_{1'}$, J$_{1',2}$=5.8); 5.79, (d, 1H, OH$_{2'}$, J$_{OH,2}$=3.5); 4.70, (m, 1H, H$_{2'}$); 4.26, (m, 1H, H$_{3'}$); 3.75, (s, 6H, OCH$_3$ of the DmTr group); 3.53, (m, 3H, H$_{4'}$, H$_{5'}$ and H$_{5''}$); 0.82, (s, 9H, tert-butyl); 0.01, (d, 6H, Me$_2$Si).

Mass spectrometry FAB>0 NOBA m/z 804 [M+H]$^+$, 303 [M+H]$^+$

General method for the preparation of the β-D-ribonucleoside phosphoramidites 26 a–d.

N,N,N-diisopropylethylamine (4 mmol, 0.7 ml), chloro-N,N-diisopropylaminomethoxyphosphine (2.5 mmol), 0.48 ml) and 4-N,N-dimethylaminopyridine (0.2 mmol, 24.4 mg) are added under an inert argon atmosphere to a solution of the 24 a–d compounds (1 mmol) in anhydrous dichloromethane (3.8 ml). The reaction mixture is stirred for 40 to 90 minutes at room temperature and is then diluted with ethyl acetate (35 ml). The resulting solution is washed with brine (4×50 ml) and then with water (2×50 ml). The organic phase is dried over sodium sulfate, filtered and evaporated under reduced pressure. The residue is chromatographed on a silica gel column and the elution is carried out by means of a mixture of cyclohexane, dichloromethane and triethylamine (100/0/0.1 to 50/50/0.1). The 26 a–d products are obtained in the form of a white powder after freeze-drying in benzene.

1-[2'-O-tert-butyldimethylsilyl-3'-N,N-diisopropylmethoxyphosphoramidite-4'thio-5'-O-dimethoxytrityl-β-D-ribofuranosyl]Thymine 26 a (diastereoisomeric mixture)

Yield: 89%

$^{31}$P NMR (CD$_3$CN): δ151.32 and 150.03.

$^1$H NMR: δ7.99, (s, 1 H, NH); 7.65, (d, 1 H, H$_6$); 7.35–6.80, (m, 13 H, aromatic H); 5.97, (m, 1 H, H$_{1'}$); 4.25, (m, 1 H, H$_{2'}$); 4.13, (m, 1H, H$_{3'}$); 3.78, (s, 6 H, OMe); 3.68, (m, 1 H, H$_{4'}$); 3.54, (m, 2 H, H$_{5'}$, H$_{5''}$); 3.35 (m, 3 H, MeO of the phosphoramidite group); 3.25, (m, 2 H, CH of the isopropyl groups); 1.60, (m, 3 H, CH$_3$); 1.15, (m, 12 H, CH$_3$ of the isopropyl groups); 0.86, (s, 9 H, tert-butyl); 0.05, (m, 6 H, Me$_2$Si); mass spectrometry FAB>0 NOBA m/z=852 [M+H]$^+$ 1-[2'-O-tert-butyldimethylsilyl-3'-N,N-diisopropylmethoxyphosphoramidite-4'-thio-5'-O-dimethoxytrityl-β-D-ribofuranosyl]Uracil 26 b (diastereoisomeric mixture)

Yield: 78%

$^{31}$P NMR (CDCl$_3$): δ150.65 and 150.50.

$^1$H NMR: (CD$_3$CN, 250 MHz): δ7.99, (s, 1 H, NH); 7.22, (m, 1 H, H$_6$); 7.30–6.89, (m, 13 H, aromatic H of the DmTr group); 5.90, (m, 1H, H$_{1'}$); 5.50, (m, 1 H, H$_5$); 4.13, (m, 2 H, H$_{2'}$, H$_{3'}$); 3.80, (s, 6 H, OMe of group DmTr); 3.58, (m, 3 H, H$_{4'}$, H$_{5'}$, H$_{5''}$); 3.42, (m, 2 H, 2 CH of isopropyl groups); 3.30, (m, 3 H, MeO of the DmTr group); 1.19, (m, 12 H, CH$_3$ of isopropyl groups); 0.84, (s, 9 H, tert-butyl); 0.05, (m, 6 H, Me$_2$Si).

Mass spectrometry FAB>0 NOBA m/z=534 [M+H-DmTrH]$^+$

1-[2'-O-tert-butyldimethylsilyl-3'-N,N-diisopropylmethoxyphosphoramidite-4'thio-5'-O-dimethoxytrityl-β-D-ribofuranosyl]-N4-benzoylCytosine 26 c.

Yield: 75%

$^{31}$P NMR (CD$_3$CN): δ151.30 and 150.05.

Mass spectrometry FAB>0 PEG m/z 941 [M+H]$^+$, 637 [M+H-DmTrH], 303 [DmTr]$^+$

1-[2'-O-tert-butyldimethylsilyl-3'-N,N-diisopropylmethoxyphosphoramidite-4'thio-5'-O-dimethoxytrityl-β-D-ribofuranosyl]-N6-benzoylAdenine 26 d.

Yield: 71%

$^{31}$P NMR (CDCl$_3$): δ151.26 and 150.01

Mass spectrometry FAB>0 PEG m/z 964 [M+H]$^+$, 600 [M+H-DmTrH], 303 [DmTr]$^+$

II.3 Functionalization of the Solid Support (Scheme 10)

The solid support or LCA-CPG (Long Chain Alkylamine Controlled Pore Glass) P-1 was first activated by a 3% trichloroacetic acid solution in dichloromethane at room temperature for 2 to 3 hours in order to liberate the highest number of amino groups, which leads to the maximum number of reactive sites on the surface of the glass beads. The thus activated support P-2 is then functionalized by coupling with succinic anhydride in pyridine in the presence of 4-DMAP, which leads to P-3.

In the following step, the 3'-silylated nucleoside 25 is used since it was obtained during the reaction for silylation of the thioribonuleosides and is not necessary for the synthesis of oligothionucleotides containing the 3'-5' phosphodiester bond. Thus, P-3 activated by 1-(3-dimethylaminopropyl)-3-ethylcarbodiimide (DEC) in the presence of 4-DMAP is reacted in anhydrous pyridine with 5'-O-DmTr-3'-OTBDMS-β-D-thioribonucleoside 25. The unused sites of the support are masked by means of piperidine. A final step of masking with acetic anhydride in the presence of collidine in THF leads to P-6. The quantity of nucleoside attached to the support is determined by UV spectrophotometryby measuring the quantity of dimethoxytrityl cation liberated after a treatment with a 10% solution of trichloroacetic acid in dichloromethane. The degree of functionalization varies from 21 to 38 μmol per gram of support depending on the nature of the nucleoside base.

SCHEME 10

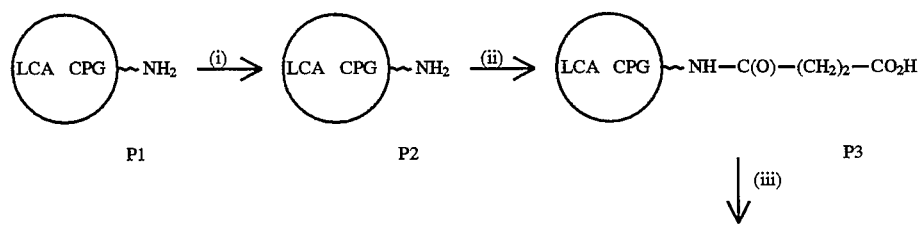

-continued
SCHEME 10

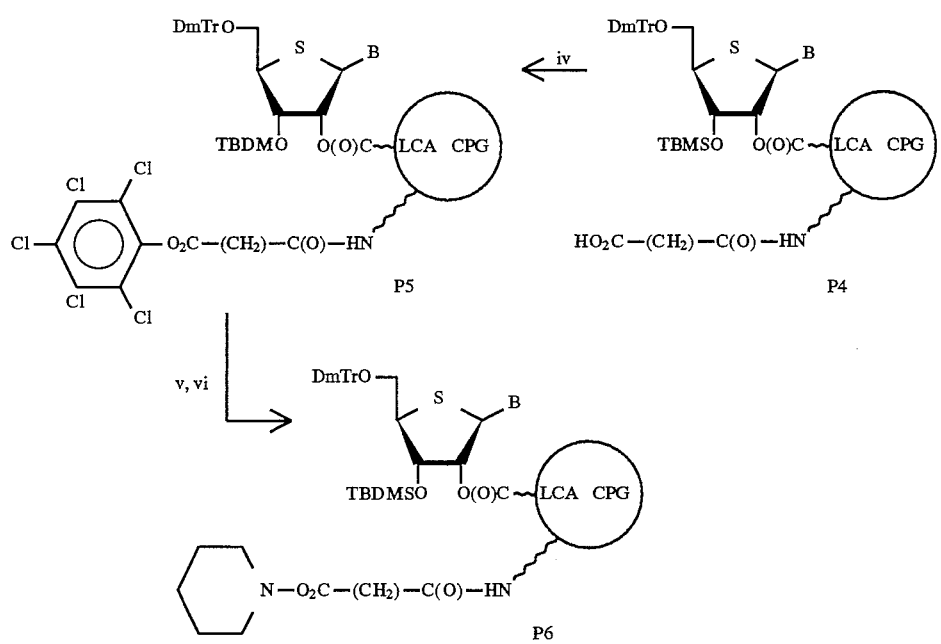

(i = TCA3%, CH$_2$Cl$_2$; ii = succinic anhydride, DMAP, Pyr;
iii = 5'-0-DmTr-4'-thio-3'-o-TBDMS-β-D-ribonucleoside,
DMAP, NEt$_3$, DEC Pyr; iv = pentachlorophenol,
v = piperidine; vi = Ac$_2$O 0.5M in THF)

II.4. Automated Synthesis of the Thiooligonucleotides (Scheme 11)

The thiooloigonucleotides were synthesized in a DNA synthesizer (Applied Biosystems model 381 A). The elongation cycle comprises four major steps:

Detritylation of the nucleoside or of the oligonucleotide attached to the solid support.

Condensation of the phosphoramidite activated by tetrazole with the free 5'-hydroxyl of the nucleoside or of the oligonucleotide.

Masking of the 5'-hydroxyl functional groups which have not reacted.

Oxidation of the phosphite triester functional groups into phosphotriester.

SCHEME 11 - DEPROTECTION AND DETACHMENT

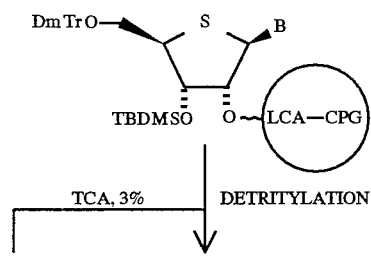

-continued
SCHEME 11 - DEPROTECTION AND DETACHMENT
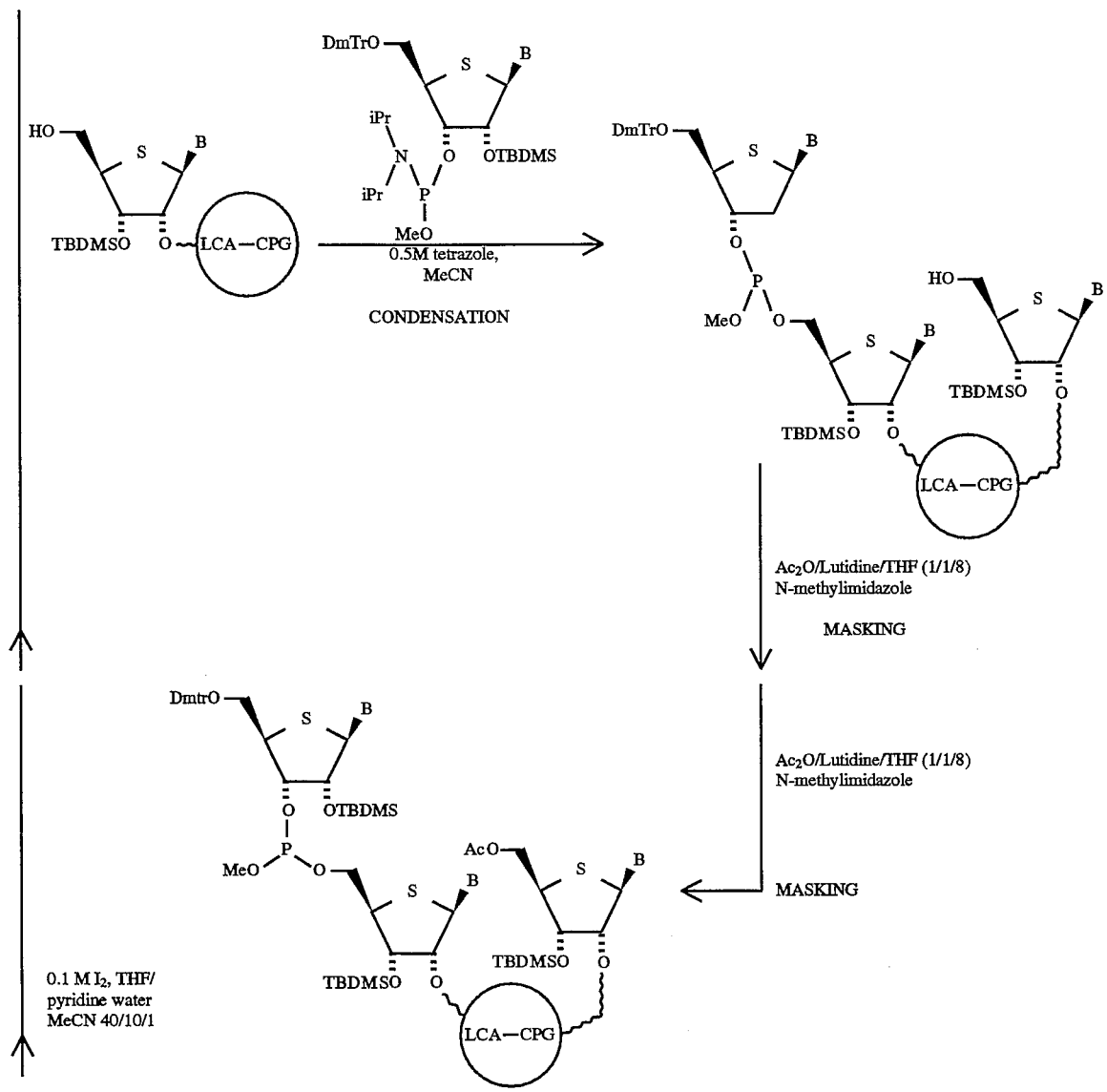

-continued
SCHEME 11 - DEPROTECTION AND DETACHMENT

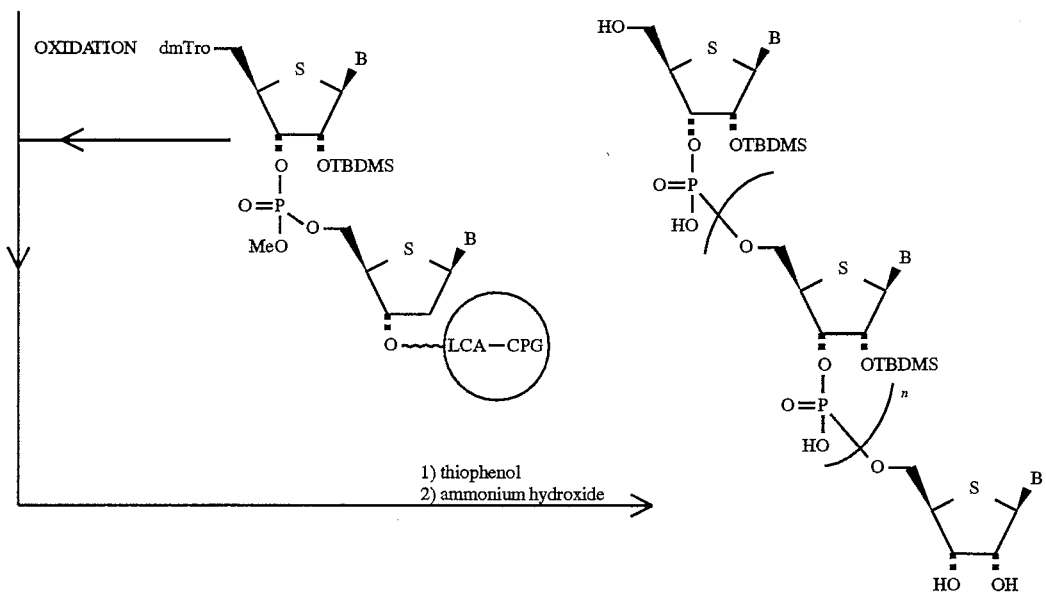

Each synthesis was carried out on a column containing 40 mg of solid support. The yield of each incorporation is 98%, evaluated by measuring the concentration of the dimethoxytrityl cations recovered after each coupling by treating the support with trichloroacetic acid.

Washes are carried out between each step and the duration of an elongation cycle is 21.1 minutes for the synthesis of the homododecamer 4'-thio-β-D-ribonucleotide (βrSU$_{12}$) (Table 1).

TABLE 1

Elongation cycle used for the synthesis of βrSU$_{12}$.

| Number | Step | Time (sec.) | Solvent and reagents |
|---|---|---|---|
| 1 | Drying and washing | 24 | MeCN-Argon |
| 2 | Detritylation | 80 | 3% TCA in CH$_2$Cl$_2$ |
| 3 | Drying and washing | 74 | MeCN-Argon |
| 4 | Coupling | 915 | amidite 0.1M (24 eq)-MeCN+tetrazole 0.5M (10 eq)+MeCN |
| 5 | Drying | 45 | Argon |
| 6 | Masking | 23 | Methylimidazole-THF Ac$_2$O/-lutidine/THF 118 |
| 7 | Drying | 11 | Argon |
| 8 | Oxidation | 43 | 0.1M I$_2$ in THF Pyr H$_2$O 40/10/1 |
| 9 | Washing | 53 | MeCN |

II.5. Detachment, Deprotection and Purification of the Thiooligomer

After carrying out the steps of deprotection of the methoxyphosphate diesters with thiophenol, the detachment of the dodecamer from the solid support by ammonium hydroxide and the deprotection of the hydroxyls by TBAF, the thiooligomer was desalted on a G-25 DEAE Sephadex exclusion column or on an A-25 Sephadex DEAE ionic column and purified by reverse-phase HPLC.

II.6 EXPERIMENTAL PART

Example I

Synthesis of the Homododecamer βrSU$_{12}$

I-1 Synthesis of the solid support:

The solid support P-1 (2.415 g) is suspended with a 3% solution (50 ml) of trichloroacetic acid in anhydrous CH$_2$Cl$_2$. After stirring for 4 h 15 min, 50 ml of a solution of triethylamine and diisopropylamine (9:1) is added and after stirring for 5 min, the solution is filtered. The solid support P-2 thus obtained is washed with dichloromethane (2×50 ml) and then with ether (50 ml) and left to dry.

The solid support P-2 is then suspended in anhydrous pyridine (14.5 ml) in the presence of succinic anhydride (0.48 g) and DMAP (0.0805 g). The suspension is stirred for 20 hours and then filtered. The solid support P-3 is then washed with anhydrous pyridine (50 ml), dichloromethane (2×50 ml) and ether (2×50 ml) and then left to dry under vacuum.

Condensation of the solid support P-3 with 1-[3'-O-tert-butyldimethylsilyl-2'-hydroxy-4'-thio-5'-O-dimethoxytrityl-β-D-ribofuranosyl]Uracil 25 b A mixture of P-3 (2.415 g), 1-[3'-O-tert-butyldimethylsilyl-2'-hydroxy-4'-thio-5'-O-dimethoxytrityl-β-D-ribofuranosyl]Uracil 25 b (333 mg, 1 eq.), DMAP (29.5 mmg, 0.5 eq.), triethylamine (0.146 mg, 202 µl, 0.003 eq.) and DEC (920 mg, 10 eq.) in 29 ml of anhydrous pyridine is stirred for 3 days at room temperature. Pentachlorophenol (321 mg, 2.5 eq.) is then added and the mixture is kept stirring for an additional 24 hours. The solid support is then filtered, rinsed with anhydrous pyridine (2×50 ml) and then with dichloromethane (2×50 ml) and ether (2×50 ml). Immediately afterwards, the solid support P-5 is treated with 25 ml of piperidine. After stirring at room temperature for 24 hours, the solid support is filtered, washed with dichloromethane (2×50 ml) and then with ether (2×50 ml) and left to dry under vacuum. The dry solid support (2,415 g) is brought into contact with a solution of acetic anhydride (0.5M) in THF (15 ml) and with a solution of collidine (0.5M) in THF (15 ml). After reacting for 4 hours, the solid support is washed with anhydrous pyridine (2×50 ml), dichloromethane (2×50 ml), THF (2×50 ml) and ether (2×50 ml). P-6 thus obtained is left to dry under vacuum.

I-2) Determination of the Level of Functionalization of the Solid Support P-6

This determination is carried out by assaying the DmTr groups liberated in an acidic medium. 38.0 mg of P-6 are weighed exactly and suspended in 3.4 ml of a solution of para-toluenesulfonic acid (0.1M) in acetonitrile. The mixture is stirred for 15 min and then sonicated for 2 min.

The volume is then adjusted to 10 ml with the 0.1M solution of para-toluenesulfonic acid in acetonitrile. 0.3 ml of this solution is removed to which 5 ml of 0.1M para-toluenesulfonic acid solution are added. The OD reading (0.317 unit of OD) at 500 nm allows us to calculate the degree of functionalization of the support P-6 which is in this case 21 µmol/gram of solid support.

I-3) Automated Synthesis of the Homododecamer $\beta rSU_{12}$

The synthesis is carried out on a column containing 39.8 mg of solid support functionalized at 21 µmol/g of resin, that is to say 0,835 µmol (1 eq) of 4'-thiouridine.

Each elongation cycle requires an excess of phosphoramidite synthon (20 µmol, 24 eq), that is to say 240 µmol in total for the synthesis of the docedamer. The synthesizer collecting 200 µl of a 0.1M solution of synthon in acetonitrile by incorporation.

The duration of an elongation cycle is 21.1 min (Table 1).

The coupling step was cosiderably increased (900 s against 45 s in the case of a deoxynucleoside) because of the lower reactivity of the ribonucleotide synthon. The assay of the liberated dimethoxytrityl cations at each detritylation step made it possible to evaluate the average yield of incorporation of the thioribonucleotide unit at 98.7%.

I-4) Detachment, Deprotection and Purification of the Thiohomododecamer $\beta rSU_{12}$ The solid support carrying the thiohomododecamer $\beta rSU_{12}$ is treated with 5 ml of a thiophenol, triethylamine, 1,2-thioxane solution (1/2/2) for half an hour at room temperature. The thiophenol solution is then filtered and the support washed with a 32% solution of ammonium hydroxide in 95% ethanol (3/1: v/v) (3×500 µl) in order to detach the thiohomododecamer from the solid support. The solution thus obtained is evaporated, taken up in 500 µl of water and then freeze-dried. The oligomer is then dissolved in 300 µl of a solution of TBAF (1.1M) in THF. The reaction mixture is kept stirring for 24 hours. The reaction is then stopped with 300 µl of an aqueous ammonium acetate solution (0.05M).

The solution is evaporated to dryness, coevaporated 3 times with water and the residue chromatographed on a Sephadex G-25 exclusion gel column. The fractions containing the thiooligomer are combined, evaporated to dryness and analyzed by HPLC. Analysis and purification of the thiooligomer $\beta rSU_{12}$ obtained.

HPLC analysis of the thiooligomer was carried out on a Beckman C-18 RP 3µ×LODS Ultrasphere column under the following gradient conditions:
A: 10% acetonitrile in a 0.05M aqueous triethyl-ammonium acetate solution B: 15% acetonitrile in a 0.05M aqueous triethyl-ammonium acetate solution:

$$A-B-B-A$$
$$20'\ 10'\ 5'$$

Analysis time: 30'.

Under these conditions, it is observed that the thiooligomer is 92.73% pure.

Purification of $\beta rSU_{12}$ is then carried out on a Nucleosyl semi-preparative column with a gradient:

$$A-B-B-A$$
$$15'\ 10'\ 5'$$

$\beta rSU_{12}$ is obtained under these conditions with a 94.42% purity which is sufficient for the subsequent studies.

Example II

Synthesis of the Dodecamer $\beta\ (SrT)_1\ dT_{11}$

II-1) Synthesis of the Solid Support

The functionalized solid support at 1 µmol per 35 mg of 2'-deoxythymidine resin as well as the synthons 1-[5'-O-DmTr-3'-O-N,N-diisopropylaminocyanoethyphosphine, 2'-deoxy-$\beta$-D-ribofuranosylthymine are marketed by Applied Biosystems.

II-2) Automated Synthesis of $\beta(SrT)_1\ dT_{11}$

The synthesis is carried out on a column containing 35 mg of solid support, that is to say 1 µmol of 2'-deoxythymidine. Each elongation cycle requires an excess of phosphoramidite synthons (20 µmol, 20 eq) that is to say 220 µmol of 2'-deoxythymidine synthons and 20 µmol of synthon 4'-thiothymidine 5. The synthesizer collecting 200 µmol by incorporation of a 0.1M solution of each synthon in acetonitrile. The duration of a cycle for incorporation of a deoxythymidine unit is 5.5 min. Whereas it is 20.1 min for a cycle for incorporation of the synthon 4'-thiothymidine.

The increase in the duration of the cycle for incorporation of the chimeric synthon is due to the coupling step of 909' against 36' for the synthon 2'-deoxythymidine.

The assay of the liberated dimethoxytrityl cations at each detritylation step made it possible to evaluate the average yield of incorporation of the 2'-deoxythymidine unit at 98.5% and 93.5% for the synthon 4'-thiothymidine.

II-3) Detachment, Deprotection and Purification of $\beta(SrT)_1\ dT_{11}$ (SEQ ID NO: 3)

The solid support carrying the $\beta\ (SrT)_1\ dT_{11}$ (SEQ ID NO: 3) oligomer is treated with a solution of ammonium hydroxide (32%) in 95% ethanol (3/1, v/v) (3×500 µl) for 3 cycles of 20 min each so as to detach the oligomer from its support, then the dodecamer is incubated for 2 h in a dry oven in the same mixture so as to deprotect the cyano-ethyl and methoxy functional groups.

The oligomer is then evaporated under vacuum, taken up in 500 µl of water and freeze-dried.

The deprotection of the TBDMS groups is carried out according to the procedure developed in Example I. The residue obtained is chromatographed on a DEAE Sephadex A-25 gel column. The fractions containing the oligomer are combined, evaporated to dryness and analyzed by HPLC.

Analysis and purification of the $\beta(SrT)_1\ dT_{11}$(SEQ ID NO: 3) by HPLC. HPLC analysis of the oligomer was carried out on a Beckman C 18 RP 3 μ Ultrasphere column under the following gradient conditions:

A: 6% acetonitrile in a 0.05M triethylammonium acetate buffer.

B: 20% acetonitrile in a 0.05M triethylammonium acetate buffer

A—B—B
15'  10'

Analysis time: 25 min.

Under these conditions, the oligomer is 49.3% pure. A purification of β(SrT)$_1$ dT$_{11}$(SEQ ID NO: 3) is then carried out by semi-preparative HPLC with a nucleosyl column under the following gradient conditions:

A—B—B
15'  5'

The 12-mer then has a retention time of 12.99 min and a purity greater than 99%.

II.4.: Synthesis of the Dodecamer βdT$_5$ (SrT) dT$_6$ (SEQ ID NO: 3)

II-4.1) Synthesis of the Solid Support

The solid support defined in Example II was used.

II-4.2) Automated Synthesis of βdT$_5$ (SrT) dT$_6$ (SEQ ID NO: 3)

The same synthesis conditions developed for the synthesis of β(SrT)$_1$ dT$_{11}$(SEQ ID NO: 3) were used.

The assay of the liberated dimethoxytrityl cations at each detritylation step made it possible to evaluate the average yield of incorporation of the 2'-deoxythymidine unit at 99.3% and at 96.1% for the synthon 4'-thiothymidine.

II-4.3) Detachment and Purification of the βdT$_5$ (SrT) dT$_6$(SEQ ID NO: 3)

The treatment of this oligomer was carried out according to the procedure developed in Example II. Analysis and the HPLC purification, carried out under the same gradient conditions, reveals a retention time of 13.18 minutes and a spectrophotometric purity at 260 mm of 100%.

III. AUTOMATED SYNTHESIS OF 4'-THIOOLIGORIBONUCLEOTIDES AND MIXED OLIGOMERS

The synthesis of a homogenous 4'-thioribo oligomer 1 directed on the acceptor splicing sequence of the HIV tat gene is described. It is shown that it is then possible to obtain mixed oligomers comprising a limited sequence of DNA having phosphodiester (sequence 4) or phosphorothioate (sequence 5) bonds.

Such mixed sequences 5'-(4'-S-RNA/DNA/4'-S-RNA)-3' 4 and 5 can be used in an antisense approach and are capable of being highly selective insofar as the "window" of the DNA structure will be the only substrate for the RNAse H after pairing of the antisense with a complementary target. It should be noted that the DNA "window" (phosphodiester or phosphorothioate) may be of variable length—in the sequences 4 and 5, there are six deoxynucleotides—and this "window" may be included at any position of the oligomer, even at the 5' and/or 3' ends.

Complementarily, this possibility opens the way to the design of artificial ribozymes (homogeneous or otherwise) containing oligo-ribonucleotide sequences 4'-S-RNA A number of homogeneous 4'-thiooligoribonucleotides (4'-S-RNA) were synthesized on a DNA synthesizer (Applied Biosystems model 381A) using the general procedure described above.

This is the case especially:

for 4'-Sr-(A-C-A-C-C-C-A-A-U-U-C-U)1SEQ ID NO: 1 for 4'-Sr-(U-U-U-U-U-U). (4'-SrU$_6$)2 and for 4'-Sr-(U-U-U-U-U-U-3'-P-CH$_2$-CH$_2$-OH), (4'-SrU$_6$-3'n-prOH)3

The expression 4'-Sr means: oligoribonucleotide of β configuration where the oxygen of the furanose ring of the sugars is replaced with a sulfur atom. 3'n-prOH means that an n-propanol functional group is attached to the phosphate group introduced at the 3' end of the oligoribonucleotide.

Furthermore, mixed oligomers comprising phosphodiester or phosphorothioate oligodeoxynucleotide sequences were obtained and the modifications made to the elongation cycle are described, taking the following sequences as example 4'-Sr—(U—U—U)-d(T—T—T—T—T—T)-4'-Sr—(U—U—U)/P$_{11}$, SEQ ID NO:2
[4'-SrU$_3$-dT$_6$-4'-SrU$_3$/P$_{11}$]4 and

4'-Sr—(U—U—U)-d(T—T—T—T—T—T)-4'-Sr—(U—U—U)/P$_3$PS$_5$P$_3$,
[4'-SrU$_3$-dT$_6$-4'-SrU$_3$/P$_3$PS$_5$P$_3$]5 where 4'-Sr has already been defined as above, P$_x$ corresponds to the number of phosphodiester bonds between the nucleotide units and PS$_y$ to the number of phosphorothioate bonds between the nucleotide units. The thiooligoribonucleotides were synthesized on a DNA synthesizer (Applied Biosystems model 381 A).

III-1) Synthesis of the 4'-thiooligoribonucleotides

4'-Sr-(A-C-A-C-C-C-A-A-U-U-C-U) (SEQ ID NO: 1) 1, 4'-SrU$_6$ 2, and 4'-SrU$_6$-3'n-prOH 3

The elongation cycle comprises four major steps:

a) Detritylation of the nucleoside or oligonucleotide attached to the solid support in the case of 4'-SrU$_6$ and 4'-Sr-(A-C-A-C-C-C-A-A-U-U-C-U) (SEQ ID NO: 1), or alternatively detritylation of the n-propanol arm attached to the solid support or of the oligonucleotide attached to the n-propanol linkage in the case of 4'-SrU$_6$-3'n-prOH.

b) Condensation of the phosphoramidite activated by tetrazole with the free 5' hydroxyl of the nucleoside or of the oligonucleotide in the case of 4'-SrU$_6$ and 4'-Sr-(A-C-A-C-C-C-A-A-U-U-C-U) (SEQ ID NO: 1), or alternatively with the free hydroxyl of the n-propanol arm or with the hydroxyl in 5' of the oligonucleotide in the case of 4'-SrU$_6$-3'n-prOH.

c) Masking of the 5'-hydroxyl functional groups which have not reacted.

d) Oxidation of the phosphite triester functional groups into phosphotriester.

Each synthesis was carried out on a column containing 40 mg of solid support. The yield of each incorporation is 98% evaluated by measuring the optical density of the dimethoxytrityl cations liberated after each coupling by treating the support with trichloroacetic acid. Washes were carried out between each step and the duration of an elongation cycle is 21.46 minutes for the synthesis of the three abovementioned oligomers. (Table 2).

TABLE 2

Elongation cycle used for the synthesis of 4'-Sr-
(A-C-A-C-C-C-A-A-U-U-C-U) (SEQ ID NO:1) 1, 4'-SrU$_6$ 2,
4'-SrU$_6$-3'n-prOH, 3

| STEPS | TIME (seconds) | SOLVENTS AND REAGENTS |
|---|---|---|
| Washing-drying | 25 | CH$_3$CN/ARGON |
| Coupling | 915 | 0.1M phosphoramidite nucleoside (20 eq.) in CH$_3$CN + 0.5M tetrazole (10 eq.) in CH$_3$CN. |
| Washing-drying | 41 | CH$_3$CN/ARGON |
| Oxidation | 36 | I$_2$ (0.1M) in THF/Pyr H$_2$O (40/10/1). |
| Washing-drying | 59 | CH$_3$CN/ARGON |
| Masking | 23 | Methylimidazole-THF 1 Ac$_2$O/lutidine/THF: 1/1 8 1 |
| Washing-drying | 71 | CH$_3$CN/ARGON |
| Detritylation | 98 | 3% TCA in CH$_2$Cl$_2$ |
| Washing-drying | 33 | CH$_3$CN/ARGON |

III-2) Synthesis of the Mixed Oligomers

4'-SrU$_3$-dT$_6$-4'-SrU$_3$/P$_{11}$ (SEQ ID NO: 2) 4 and 4'-SrU$_3$-dT$_6$-4'-SrU$_3$/P$_3$PS$_5$P$_3$.

III-2-1 Oligonucleotide 4'-SrU$_3$-dT$_6$-4'-SrU$_3$ P$_{11}$ (SEQ ID NO: 2) 4.

The automated synthesis of this oligonucleotide follows the four steps described in II-1. Each synthesis was carried out on a column containing 40 mg of solid support. The yield of each incorporation is 98%. The duration of a cycle for elongation by the monomer 4'-Sr-U is 21.43 minutes against 6.73 minutes for a dT monomer. This difference is due to the increase in the coupling time for an entity 4'-Sr-U which is 915 seconds against 36 seconds for a dT unit (Table 3).

TABLE 3

Elongation cycle used for the synthesis of
4'-SrU$_3$dT$_6$-4'-SrU$_3$/P$_{11}$ (SEQ ID NO:2) 4.

| STEPS | TIME (seconds) | SOLVENTS AND REAGENTS |
|---|---|---|
| Washing-drying | 25 | CH$_3$CN/ARGON |
| Coupling 4'-Sr-U | 915 | 0.1M phosphoramidite |
| dT | 36 | nucleoside (20 eq.) in CH$_3$CN + 0.5M tetrazole (10 eq.) in CH$_3$CN. |
| Washing-drying | 41 | CH$_3$CN/ARGON |
| Oxidation | 36 | I$_2$ (0.1M) in THF/Pyr/H$_2$O (40/10/1). |
| Washing-drying | 59 | CH$_3$CN/ARGON |
| Masking | 23 | Methylimidazole-THF 1 Ac$_2$O/lutidine/THF: 1/1/8 1 |
| Washing-drying | 71 | CH$_3$CN/ARGON |
| Detritylation | 98 | 3% TCA in CH$_2$Cl$_2$ |
| Washing-drying | 33 | CH$_3$CN/ARGON |

III-2-2 Oligonucleotide 4'-SrU$_3$-dT$_6$-4'-SrU$_3$ P$_3$PS$_5$P$_3$, (SEQ ID NO: 2) 5

The same automated synthesis conditions were applied to this mixed dodecamer containing both phosphodiester and phosphorothioate bonds.

The synthesis was carried out on a scale of one µmol, that is to say on a column containing about 40 mg of solid support functionalized at 21 µmol/g. The average yield of incorporation is 98%.

During the introduction of an internucleotide bond of the phosphorothioate type, the oxidation step defined in paragraph IV-2-1 (Step 4, Table 3) was replaced by a sulfurization step of 51 seconds using the Beaucage reagent ("derivatives of benzenesulfone carboxythioanhydride") dissolved in acetonitrile at a concentration of 0.05M.

The other steps of the elongation cycle remain unchanged.

III-3 Detachment, Deprotection and Purification of the 4'-thiooligoribonucleotides (4'-S-RNA)

After having carried out the steps of deprotection of the methoxyphosphotriesters to phosphodiesters by treating with thiophenol, the 4'-thiooligoribonucleotides were separated from the solid supports by a treatment with ammonium hydroxide. The TBDMS groups introduced into the hydroxyls in 2' were deprotected by a solution of TBAF in THF. The thiooligomers were then desalted on a DEAE Sephadex G-25 exclusion column and then purified by reversed-phase HPLC.

III-4 EXPERIMENTAL PART

Example I

Synthesis of the hexamers: 4'-SrU$_6$ 2 and 4'-SrU$_6$-3'n-prOH, 3.

I-1 Synthesis of the Solid Supports

The solid support necessary for the synthesis of 4'-SrU$_6$, 2 is the same as that used for the synthesis of βrSU$_{12}$. The synthesis of 4'-SrU$_6$-3'n-prOH 3requires the use of the universal solid support:

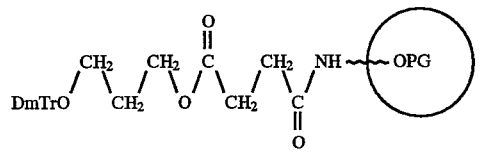

From the intermediate P-3 described in Patent No. 92 01275, a mixture of 1-O-DmTr-3-propanol (1 eq.), DMAP (29.5 mg, 0.5 eq.), triethylamine (0,146 mg, 0.003 eq.), DEC (920 mg, 10 eq.) and P-3 (2.415 g) is stirred in 29 ml of anhydrous pyridine for three days at room temperature. Pentachlorophenol (321 mg, 2.5 eq.) is added and the stirring of the reaction mixture is continued for an additional 24 hours. The solid support is then filtered, rinsed with anhydrous pyridine (2×50 ml) and then with dichloromethane (2×50 ml) and ether (2×50 ml).

The solid support is then treated with piperidine, and then with a solution of acetic anhydride and collidine in THF according to the procedure defined above.

I-2) Determination of the Level of Functionalization of the Solid Support

This determination was carried out using the procedure described above. The level of functionalization of the solid support was evaluated at 16.4 µmol of n-propanol per gram of resin.

I-3-) Automated Synthesis of the Hexamers 4'-SrU$_6$ 2 and 4'-SrU$_6$-3'n-prOH 3

I-3-1) Automated Synthesis of the Hexamer 4'-SrU$_6$ 2

The synthesis was carried out on a column containing 39.4 mg of solid support functionalized at 21 µmol/g of resin, that is to say 0,827 µmol (1 eq.) of 4'-thiouridine. Each elongation cycle requires an excess of phosphoramidite synthon (16.75 µmol, 20.3 eq.) that is to say 100.5 µmol in total in a 0.1M solution in acetonitrile. The duration of the elongation cycle defined in Table 1 is 21.46 minutes.

The assay of the dimethoxytrityl cations liberated at each detritylation step made it possible to calculate the average yield of incorporation of a thioribonucleotide unit at 98.3%.

I-3-2) Automated Synthesis of the Hexamer 4'-SrU$_6$-3'n-prOH 3

The synthesis is carried out on a column containing 36.2 mg of solid support functionalized at 16.4 µmol of n-propanol per gram of resin, that is to say 0.82 µmol (1 eq.) of n-propanol.

The total synthesis of 4'-SrU$_6$-3'n-prOH, 3 requires 95.9 mg of phosphoramidite synthon (114.8 µmol, 20 eq.) dissolved in 1.14 ml of acetonitrile. The duration of an elongation cycle is 21.46 minutes. The average yield per coupling is 98.3%.

I-4) Detachment, Deprotection and Purification of 4'-SrU$_6$ 2 and 4'-SrU$_6$-3'n-prOH 3

The treatment using successively thiophenol, ammonium hydroxide and a solution of TBAF common to the two hexamers is described above.

I-4-1) Analysis and Purification of the Hexamer 4'-SrU$_6$ 2

HPLC analysis of the thiooligomer was carried out on an SFCC Nucleosyl C-18 N125 2P 789 column under the following gradient conditions:
A: 10% acetonitrile in a 0.05M aqueous solution of triethylammonium acetate
B: 15% acetonitrile in a 0.05M aqueous solution of triethylammonium acetate $$A \xrightarrow{-20'} B \xrightarrow{-10'} B$$

Analysis time: 30 minutes, flow rate: 1 ml/min. Under these conditions, the hexamer 4'-SrU$_6$, 2 has a spectrophotometric purity at 260 nm of 95.3%.

A preparative HPLC purification on a semi-preparative nucleosyl column with a flow rate of 2 ml/min and an isocratic eluent of 12% acetonitrile in a 0.05M aqueous solution of triethylamunoniumacetate enabled us to obtain 4'-SrU$_6$, 2 with a spectroscopic purity of 97.7%.

I-4-2) Analysis and Purification of the Hexamer 4'-SrU$_6$-3'n-prOH 3

The analysis was carried out under the same column and gradient conditions as for the hexamer 4'-SrU$_6$.

The 4'-SrU$_6$-3'n-prOH, 3 was obtained with a spectroscopic purity at 260 nm of 51.6%. This purity increases to 92% after purification by preparative HPLC carried out in a 10% to 13% gradient of acetonitrile in a 0.05M aqueous solution of triethylammonium acetate in 50 minutes, followed by a plateau at 13% acetonitrile in a 0.05M aqueous solution of triethylammonium acetate for 10 minutes.

Example II

Synthesis of the Mixed Dodecamer

4'-SrU$_3$-dT$_6$-4'-SrU$_3$/P$_{11}$(SEQ ID NO: 2) 4

II-1) Synthesis of the Solid Support

The solid support used for this synthesis is identical to that required for the synthesis of βrSU$_{12}$(SEQ ID. NO: 5)

II-2) Automated Synthesis of 4'-SrU$_3$-dT$_6$-4'-SrU$_3$/P$_{11}$(SEQ ID NO: 2) 4

The synthesis of the dodecamer is carried out on a column containing 39.3 mg of solid support, that is to say 0,819 µmol of 4'-thiouridine. Each elongation cycle requires an excess of 4'-thiouridine phosphoramidite synthons (16.75 µmol, 20.3 eq.) that is to say 100.5 µmol of 4'-thiouridine synthons dissolved in 1.2 ml of acetonitrile (0,083M) and an excess of deoxythymidine phosphoramidite synthon (20 eq., 16.38 µmol) that is to say 98.28 µmol of dT in a 0.1M solution in acetonitrile. The duration of a cycle for incorporation of a deoxythymidine unit is 6.73 min, whereas it is 21.43 min for a cycle for incorporation of the synthon 4'-thioribouridine.

The assay of the liberated dimethoxytrityl cations at each detritylation step made it possible to evaluate the average yield of incorporation at 98.0%.

II-3) Detachment, Deprotection and Purification of the 4'-SrU$_3$-dT$_6$-4'-SrU$_3$/P$_{11}$(SEQ ID NO: 2) 4

The steps for detachment of the oligomer from the solid support and for deprotection of the internucleotide phosphotriester bonds with thiophenol are identical to those described in Example 1.

II-3-1) Analysis and Purifaction of the 4'-SrU$_3$-dT$_6$-4'-SrU$_3$ P$_{11}$(SEQ ID NO: 2) by HPLC HPLC analysis of the oligomer 4 was carried out on an SFCC Nucleosyl C18 N125 2P789 column with a gradient at 10% to 15% acetonitrile in a 0.05M aqueous solution of triethylammonium acetate for 20 minutes (flow rate: 1 ml/min, analysis time 30 min). Under these conditions, the mixed dodecamer has a spectrophotometric purity at 260 nm of 92.5%.

A semi-preparative HPLC purification on a Nucleosyl column with a flow rate of 2 ml/min in the same gradient increases the spectrophotometric purity of the mixed sequence 4'-SrU$_3$-dT$_6$-4'-SrU$_3$/P$_{11}$ (SEQ ID NO: 2), 4 to 99.5%.

EXAMPLE III

Automated Synthesis of 4'-SrU$_3$-dT$_6$-4'-SrU$_3$/P$_3$PS$_5$P$_3$(SEQ ID NO: 2) 5

III-1) Synthesis of the Solid Support

The solid support used is the same as that described in Example I.

III-2) Automated Synthesis of 4'-SrU$_3$-dT$_6$-4'-SrU$_3$/P$_3$PS$_5$P$_3$(SEQ ID NO: 2) 5

The synthesis of the dodecamer is carried out on a column containing 39.5 mg of functionalized support, that is to say 0.831 μmol (1 eq.) of 4'-thiouridine. Each elongation cycle requires an excess of 4'-thiouridine phosphoroamidite synthon (16.75 μmol, 20.3 eq.), that is to say 100.5 μmol of 4'-Sr-U in total and an excess of 20 eq. (16.38 μmol) of deoxythymidine synthon, that is to say 98.28 μmol for the entire synthesis.

The duration of a cycle for incorporation of a deoxythymidine is 7.7 minutes against 21.43 minutes for the incorporation of a 4'-thiouridine. The assay of the liberated dimethoxytrityl cations indicates an average yield of incorporation of the synthons of 98.7%.

III-3) Detachment, Deprotection and Purification of the 4'-SrU$_3$-dT$_6$-4'-SrU$_3$/P$_3$PS$_5$P$_3$ (SEQ ID NO: 2) 5

The treatment of this oligomer is identical to that defined in Example I. Analysis and the HPLC purification, carried out on an SFCC Nucleosyl C-18 N125 2P 789 column in a gradient of 10% to 20% acetonitrile in a 0.05M aqueous solution of triethylammonium acetate for 20 minutes (flow rate: 1 ml/min, analysis time 30 min) shows a spectrophotometric purity at 260 nm of 85%.

The purification by semi-preparative HPLC on a semi-preparative Nucleosyl column with a flow rate of 2 ml/min under isocratic conditions at 19% acetonitrile in a 0.05M aqueous solution of triethylammonium acetate increases the purity of the oligomer to 99.1%.

Example IV

Synthesis of the Anti"tat" Dodecamer

4'-Sr-(A-C-A-C-C-C-A-A-U-U-C-U) (SEQ ID NO: 1) 1

IV-1) Synthesis of the Solid Support

The solid support used for this automated synthesis is identical to that described in Example I.

IV-2) Automated Synthesis of the Anti"tat" Dodecamer

4'-Sr-(A-C-A-C-C-C-A-A-U-U-C-U) (SEQ ID NO: 1) 1

The synthesis of this heterododecamer which is complementary to the splicing acceptor site of the HIV tat gene is carried out on a column containing 38.5 mg of functionalized solid support, that is to say on 0.808 μmol of 4'-thiouridine (1 eq.). Each elongation cycle uses an excess of 25.24 eq. (20.4 μmol) of 4'-thioadenosine phosphoramidite synthon, 13.5 eq. (10.97 μmol) of 4'-thiocytidine synthon and 30 eq. (24.25 μmol) of 4'-thiouridine synthon. The duration of an incorporation cycle is 20.71 minutes and the assay of the dimethoxytrityl cations indicates an average yield of incorporation of the phosphoramidite synthons of 93.6%.

IV-3) Detachment, Deprotection and Purification of 4'-Sr-(A-C-A-C-C-C-A-A-U-U-C-U) (SEQ ID NO: 1) 1

The solid support carrying the dodecamer 4'-Sr-(A-C-A-C-C-C-A-A-U-U-C-U) (SEQ ID NO: 1), 1 is treated with 5 ml of a thiophenol/triethylamine/dioxane solution (1/2/1) for half an hour at room temperature. The thiophenol solution is then filtered and the solid support is washed with 3×3 ml of methanol, and then with a 32% ammonium hydroxide solution in 95% ethanol (3/1: v/v) (3×500 μl) so as to detach the oligomer from its support. The solution obtained is incubated in a dry oven thermostated at 55° C. for 5 hours so as to deprotect the groups for protecting the heterocyclic bases. It is then evaporated, taken up in 500 μl of water and freeze-dried. The freeze-dried oligomer is then dissolved in 300 μl of a solution of TBAF (1.1M) in THF. The reaction mixture is left at room temperature for 24 hours. The reaction is then stopped with 300 μl of a 0.05M aqueous solution of ammonium acetate. The solution is evaporated to dryness, coevaporated with 3 portions of 500 μl of water and the residue is desalted on a DEAE Sephadex G-25 exclusion gel column. The fractions containing the 4'-thiooligomer are combined, evaporated to dryness, redissolved in 1.2 ml of water and filtered on a millipore filter before being analyzed by HPLC.

IV-4) Analysis and Purification of 4'-Sr-(A-C-A-C-C-C-A-A-U-U-C-U) (SEQ ID NO: 1), 1

The analytical HPLC analysis of the dodecamer 1 was carried out on an SFCC Nucleosyl C18 N125 2P789 column in a gradient of 10% to 15% acetonitrile in a 0.05M aqueous solution of triethylammonium acetate with a flow rate of 1 ml/min and an analysis time of 30 minutes. The chromatogram indicates a spectrophotometric purity at 260 nm of 44.9%. A purification by semi-preparative HPLC on a semi-preparative Nucleosyl C18 column using the same gradient with a flow rate of 2 ml/min and an analysis time of 30 minutes brings the spectroscopic purity of the 4'-Sr-(A-C-A-C-C-C-A-A-U-U-C-U) (SEQ ID NO: 1), 1 to 100%.

IV. HYBRIDIZATION PROPERTY OF THE β-4'-THIOOLIGONUCLEOTIDES

UV spectrophotometry makes it possible to study the nucleic acids and to detect the formation of duplex, the melting temperature being one of the characteristics of a duplex. The stacking and pairing of the bases of the nucleic acids are accompanied by a decrease in the UV absorbtion (hypochromicity). Thus, by UV spectrophotometry, it is possible to monitor the formation or the dissociation of a duplex (W. SANGER, *Principles of Nucleic Acid Structure*, Springer-Verlag, New York, 1984, pp. 141–149). When the temperature of a solution containing a double helix (DNA or RNA) is slowly increased, the UV absorbtion increases substantially during the entire dissociation. The point of inflection of the curve, of sygmoidal shape, of the variation of the absorbance as as function of temperature is called melting temperature or Tm and corresponds to the co-existence of separate strands and paired strands in a 50/50 ratio.

Analysis of the melting curves for the β-4'-thiooligoribonucleotide/β-oligodeoxyribonucleotide and β-4'-thiooligoribonucleotide/β-oligoribonucleotide duplexes will make it possible to define the thermal stability of such duplexes by the measurement of the melting temperature. These hybridization experiments are carried out preserving a 1/1 stoichiometry between the two complementary strands, in the presence of a 1M NaCl, 10 mM sodium cacodylate buffer. A high NaCl concentration indeed favors the pairings by solvating the negative charges around the phosphorus atoms of the two oligonucleotides. We therefore carried out these hybridization experiments in a 0.1M NaCl, 10 mM sodium cacodylate buffer.

IV.1 RESULTS AND DISCUSSION

Examples I and II

Experiments for melting the $\beta SrU_{12}$(SEQ ID NO: 5)/polyrA and $\beta rU_{12}$(SEQ ID NO: 5)/polyrA duplexes.

These experiments make it possible to demonstrate the influence of the sulfur atom in position 4' of the modified dodecamer on the thermal stability of the duplex by comparing the Tm values obtained with those for the natural duplex.

Table 4 summarizes the melting temperatures obtained in the two experiments.

TABLE 4

Melting temperatures for the dodecamer duplexes
Concentration 3 μM of each oligomer.

| Concentration of NaCl | $\beta SrU_{12}$ (SEQ ID NO:5) polyrA °C. hypochromicity % | $\beta rU_{12}$ (SEQ ID NO:5) polyrA °C. hypochromicity % |
|---|---|---|
| 1M | 46° C. 25% | in progress |
| 0.1M | 33° C. 25% | in progress |

Analysis of these results shows that the duplex $\beta SrU_{12}$(SEQ ID NO: 5)/polyrA has a good thermal stability represented by the Tm of 46° C. obtained at an NaCl concentration of 1M.

Examples III and IV

Experiments for melting of the $\beta SrU_{12}$(SEQ ID NO: 5)/$\beta dC_2A_{12}C_2$(SEQ ID NO: 4) and $\beta rU_{12}$(SEQ ID NO: 5)/$\beta dC_2A_{12}C_2$(SEQ ID NO: 4) Duplexes The melting temperatures obtained in both experiments are summarized in Table 5.

TABLE 5

Melting temperatures for the dodecamer duplexes
Concentration 3 μM of each oligomer.

| Concentration of NaCl | $\beta SrU_{12}$ (SEQ ID NO:5) $\beta dC_2A_{12}C_2$ (SEQ ID NO:4) °C. hypochromicity % | $\beta rU_{12}$ (SEQ ID NO:5) $\beta dC_2A_{12}C_2$ (SEQ ID NO:4) °C. hypochromicity % |
|---|---|---|
| 1M | 27° C. 9.3% | in progress |
| 0.1M | 5° C. 5.6% | in progress |

Example IV

Experiment for self-hybridization of the oligomer $\beta SrU_{12}$ (SEQ ID NO: 5)

In order to verify the previous results, it is necessary to ensure that the dodecamer $\beta SrU_{12}$(SEQ ID NO: 5) does not lead to any self-hybridization. For that, an experiment for self-hybridization of the dodecamer $\beta SrU_{12}$(SEQ ID NO: 5) was carried out at two NaCl concentrations (1M and 0.1M). The hybridization curves do not have the characteristic sigmoidal shape but obey the equation A=k·T where A is the absorbance at 260 nm, T the temperature and k a constant. No point of inflection can be visualized on such a straight line. We can therefore conclude that the dodecamer $\beta SrU_{12}$ (SEQ ID NO: 5) does not self-pair.

Comparison of the melting temperatures of the duplexes $\beta SrU_{12}$(SEQ ID NO: 5)/$\beta dC_2A_{12}C_2$(SEQ ID NO: 4) (Table 5) and $\beta SrU_{12}$(SEQ ID NO: 5)/polyrA (Table 4) shows a thermal stability of the RNA/RNA homoduplex (Tm=46° C.) which is substantially greater than that for the RNA/DNA heteroduplex (Tm=27° C.), moreover, no self-hybridization of $\beta SrU_{12}$(SEQ ID NO: 5) was observed.

Example VI and VII

Experiment for Melting of the $\beta dT_5(SrT)dT_6$(SEQ ID NO: 3)/$\beta dC_2A_{12}C_2$(SEQ ID NO: 4) and $\beta dT_{12}$ (SEQ ID NO: 3)/$\beta dC_2A_{12}C_2$(SEQ ID NO: 4) Duplexes This experiment makes it possible to evaluate the thermal stability of the duplex $\beta dT_5(SrT)dT_6$(SEQ ID NO: 3)/$\beta dC_2A_{12}C_2$(SEQ ID NO: 4) in comparison with that of the natural duplex $\beta dT_{12}$(SEQ ID NO: 3)/$\beta dC_2A_{12}C_2$(SEQ ID NO: 4) (FIG. 1). The melting temperatures of these duplexes are indicated in Table 6.

TABLE 6

Melting temperature of the duplexes
$\beta dT_5(SrT)dT_6$ (SEQ ID NO:3)/$\beta dC_2A_{12}C_2$ (SEQ ID NO:4)
and $\beta dT_{12}$ (SEQ ID NO:3)/$\beta dC_2A_{12}C_2$ (SEQ ID NO:4)
Concentration of each oligomer 10 μM

| Concentration of NaCl | $\beta dT_5(SrT)dT_6$/ (SEQ ID NO:3) $\beta dC_2A_{12}C_2$ (SEQ ID NO:4) °C. hypochromicity % | $\beta dT_{12}$ (SEQ ID NO:3)/ $\beta dC_2A_{12}C_2$ (SEQ ID NO:4) °C. hypochromicity % |
|---|---|---|
| 1M | 40° C. 18% | 45° C. 20.5% |

In view of these results, it appears that the thermal stability of the modified duplex is less than that of the natural duplex. However, the difference of 5° C. existing between the two melting temperatures is too low to conclude that there is a mismatch. Indeed, some authors (Y. KAWASE, S. IWAI, H. INOUE, K. MIURA and E. OKTSUKA. *Nucleic Acid Research*, 1986, 14, 7727) have shown that the existence of a single mismatch in a duplex of 13 nucleotide units results in a decrease in Tm greater than 10° C.

It can therefore be concluded that the 4'-thionucleotide pairs well with 2'-deoxyadenosine but with an affinity lower than that for 2'-deoxythymidine as confirmed by the difference in Tm of 5° C. which is obtained (Table 6).

IV.2. EXPERIMENTAL PART

General Method for the Hybridization Experiments

A—Assay of the Complementary Oligomers

In order to carry out the hybridization experiment, it is necessary to know the concentration of each oligomer in order to preserve the 1:1 stoichiometry between the two complementary strands. According to the BEER-LAMBERT law A=εlc, the absorbances of the oligomers were measured at 80° C. in order to remove the phenomenon of stacking of the bases creating a disturbance in the hyperchromicity due to the existence of tertiary structures. The molar extinction coefficients of the dodecamers at 80° C. can therefore be known according to the relationship $\epsilon^{265}(SrU_{12})=12\epsilon^{265}(rU)$ B—Hybridization Conditions The hybridization experiments were carried out with a UVIKON 810 spectrophotometer (KONTRON), coupled to an IBM-compatible microcomputer. The temperature is controlled by a HUBER PD 415 temperature programmer connected to a thermostated bath (HUMER MINISTAT). The UV cuvettes are made from quartz of 1 cm in length and a continous circulation of nitrogen is used for temperatures of less than 20° C. Before the experiment, 3 µM (Examples 1 to V) or 10 µM (Examples VI and VII) of complementary oligomers are brought into contact in a sufficient quantity for 1000 µl of 1M NaCl and 10 mM sodium cacodylate buffer, adjusted to pH 7 (Examples I to VII). This mixture is heated at 80° C. for 1 hour, and then cooled to −20° C. according to a temperature gradient of 0.5° C. per minute. The absorbance and temperature values are collected every 30 seconds.

The same experiment is carried out using a sufficient quantity for 1000 µl of 0.1M NaCl, 10 mM sodium cacodylate hybridization buffer adjusted to pH 7 in order to evaluate the thermal stability of the duplex in this buffer which favors the pairings less.

EXAMPLE I

Thermal Stability of the Duplex $\beta SrU_{12}$(SEQ ID NO: 5)/polyrA

I-1 Assay of the Oligomers

Concentration of $\beta SrU_{12}$(SEQ ID NO: 5)=0.351 mM
Concentration of polyrA=4.61 mM I-2 Hybridization Conditions 3 µM (8.55 µl) of $\beta SrU_{12}$(SEQ ID NO: 5) and 3 µM (7.79 µl) of polyrA are brought into contact with 983.6 µl of hybridization buffers (1M NaCl, 10 mM sodium cacodylate or 0.1M NaCl, 10 mM sodium cacodylate)

EXAMPLE II

Thermal Stability of the Duplex $\beta rU_{12}$(SEQ ID NO: 5)/polyrA in Progress

EXAMPLE III

Thermal Stability of the Duplex $\beta SrU_{12}$(SEQ ID NO: 5)/$\beta dC_2A_{12}C_2$(SEQ ID NO: 4)

III-1 Assay of the Oligomers

Concentration of $\beta SrU_{12}$(SEQ ID NO: 5)=0.351 mM
Concentration of $\beta dC_2A_{12}C_2$(SEQ ID NO: 4)=0.369 mM III-2 Hybridization Conditions 3 µM (8.55 µl) of $\beta SrU_{12}$(SEQ ID NO: 5) and 3 µM (8.11 µl) of $\beta dC_2A_{12}C_2$(SEQ ID NO: 4) are brought into contact with 983.3 µl of hybridization buffers (1M NaCl, 10 mM sodium cacodylate or 0.1M NaCl, 10 mM sodium cacodylate).

EXAMPLE IV

Thermostability of the Duplex $\beta rU_{12}$(SEQ ID NO: 5)/$\beta dC_2A_{12}C_2$(SEQ ID NO: 4) (in progress)

IV-1 Assay of the Oligomers

Concentration of $\beta rU_{12}$(SEQ ID NO: 5)=
Concentration of $\beta dC_2A_{12}C_2$(SEQ ID NO: 4)=0.369 mM III-2 Hybridization Conditions 3 µM (µl) of $\beta rU_{12}$(SEQ ID NO: 5) and 3 µM (8.11 µl) of $\beta dC_2A_{12}C_2$(SEQ ID NO: 4) are brought into contact with µl of the hybridization buffers (1M NaCl, 10 mM sodium cacodylate or 0.1M NaCl, 10 mM sodium cacodylate).

EXAMPLE V

Experiments for Self-hybridization of the Oligomer $\beta SrU_{12}$(SEQ ID NO: 5)

V-1 Assay of the Oligomers

Concentration of $\beta rU_{12}$(SEQ ID NO: 5)=0.351 mM

V-2 Hybridization Conditions

6 µM (17.10 µl) of $\beta SrU_{12}$(SEQ ID NO: 5) are brought into contact with 986.9 µl of hybridization buffers (1M NaCl, 10 mM sodium cacodylate or 0.1M NaCl, 10 mM sodium cacodylate).

EXAMPLE VI

Thermal Stability of the Duplex $\beta dT_5(SrT)dT_6$(SEQ ID NO: 3)/$\beta dC_2A_{12}C_2$(SEQ ID NO: 4)

VI-1 Assay of the Oligomers

Concentration of $\beta dT_5(SrT)dT_6$(SEQ ID NO: 3)=1.33 mM
Concentration of $\beta dC_2A_{12}C_2$(SEQ ID NO: 4)=0.369 mM VI-2 Hybridization Conditions 10 µM (7.49 µl) of $\beta dT_5(SrT)dT_6$(SEQ ID NO: 3) and 10 µm (22.5 µl) of $\beta dC_2A_{12}C_2$(SEQ ID NO: 4) are brought into contact with 970 µl of 1M NaCl, 10 mM sodium cacodylate hybridization buffer.

EXAMPLE VII

Thermostability of the Duplex $\beta dT_{12}$(SEQ ID NO: 3)/$\beta dC_2A_{12}C_2$(SEQ ID NO: 4)

VII-1 Assay of the Oligomers

Concentration of $\beta dT_{12}$(SEQ ID NO: 3)=1.196 mM
Concentration of $\beta dC_2A_{12}C_2$(SEQ ID NO: 4)=0.369 mM VII-2 Hybridization Conditions 10 µM (8.36 µl ) of $\beta dT_{12}$(SEQ ID NO: 3) and 10 µM (22.5 µl) of $\beta dC_2A_{12}C_2$(SEQ ID NO: 4) are brought into contact with 969.1 µl of 1M NaCl, 10 mM sodium cacodylate hybridization buffer.

V. PROPERTIES OF HYBRIDIZATION OF THE 4'-S-RNA AND MIXED OLIGOMERS

The hybridization experiments were carried out preserving the 1/1 stoichiometry between the two complementary strands in the presence of a 1M NaCl, 10 mM sodium cacodylate buffer. A high NaCl concentration indeed favors the pairings by solvating the negative charges around the phosphorus atoms of the two oligonucleotides. We carried out these hybridization experiments in another buffer 0.1M NaCl, 10 mM sodium cacodylate.

V-1-RESULTS AND DISCUSSION

Experiments for melting the duplexes:

[4'-SrU$_3$-dT$_6$-4'-SrU$_3$/P$_{11}$ (SEQ ID NO:2)]/polyrA, [4/polyrA]
[4'-SrU$_3$-dT$_6$-4'-SrU$_3$/P$_{11}$ (SEQ ID NO:2)]/d(C$_2$A$_{12}$C$_2$),
[4/d(C$_2$A$_{12}$C$_2$ (SEQ ID NO:4))]
[4'-SrU$_3$-dT$_6$-4'-SrU$_3$/P$_3$PS$_5$P$_3$ (SEQ ID NO:2)]/polyrA,
[5/polyrA]
[4'-SrU$_3$-dT$_6$-4'-SrU$_3$/P$_3$PS$_5$P$_3$ (SEQ ID NO:2)]/d(C$_2$A$_{12}$C$_2$),
[5/d(C$_2$A$_{12}$C$_2$ (SEQ ID NO:4))]

are carried out at two NaCl concentrations and make it possible to evaluate the influence of the phosphorothioate bonds on the stability of hybridization compared to the oligonucleotides with normal phosphodiester bonds (Table 7).

TABLE 7

Results of the melting experiments.

| NaCl concentration (M) | Duplex | Tm °C. |
|---|---|---|
| 1 | 4/poly rA | 45 |
| 1 | 5/poly rA | 36 |
| 1 | 4/d(C$_2$A$_{12}$C$_2$ (SEQ ID NO:4)) | 31 |
| 1 | 5/d(C$_2$A$_{12}$C$_2$ (SEQ ID NO:4)) | 19 |
| 0.1 | 4/poly rA | 32 |
| 0.1 | 5/poly rA | 24 |
| 0.1 | 4/d(C$_2$A$_{12}$C$_2$ (SEQ ID NO:4)) | 10 |
| 0.1 | 5/d(C$_2$A$_{12}$C$_2$ (SEQ ID NO:4)) | 3 |

The mixed dodecamer 5 having both internucleotide bonds of the phosphodiester and phosphorothioate type (P$_3$PS$_5$P$_3$) induces a decrease in the Tm value by about 2° C. per phosphorothioate linkage. On the other hand, the oligomer 4 has Tm values which are equivalent to those obtained for the dodecamer βrSU$_{12}$(SEQ ID NO: 5) with the two complementary sequences poly rA and d(C$_2$A$_{12}$C$_2$)(SEQ ID NO: 4). These results (Table 7) indicate that the oligomers of mixed sequence 4 and 5 have a good thermal stability with complementary RNA sequences.

EXPERIMENTAL PART

General Method for the Hybridization Experiments

A—Assay of the Complementary Oligomers

In order to carry out the hybridization experiments, it is necessary to know the concentration of each oligomer in order to preserve the 1:1 stoichiometry between the two complementary strands. According to the BEER-LAMBERT law A=εlc, the absorbances of the oligomers were measured at 80° C. in order to remove the phenomenon of stacking of the bases creating a disturbance in the hyperchromicity due to the existence of tertiary structures. The molar extinction coefficients of the dodecamers at 80° C. can therefore be known according to a relationship similar to ε$^{265}$(SrU$_{12}$)~12ε$^{265}$(SrU)

B—Hybridization Conditions

The hybridization experiments were carried out with a UVIKON 810 spectrophotometer (KONTRON), coupled to an IBM-compatible microcomputer. The temperature is controlled by a HUBER PD 415 temperature programmer connected to a thermostated bath (HUMER MINISTAT). The UV cuvettes are made from quartz of 1 cm in length and a continous circulation of nitrogen is used for temperatures of less than 20° C. Before the experiment, 3 μM (Examples 1 to IV) of complementary oligomers are brought into contact in a sufficient quantity for 1000 μl of 1M NaCl and 10 mM sodium cacodylate buffer, adjusted to pH 7 (Examples I to VII). This mixture is heated at 80° C. for 1 hour, and then cooled to −20° C. according to a temperature gradient of 0.5° C. per minute. The absorbance and temperature values are collected every 30 seconds. The same experiment is carried out using a sufficient quantity for 1000 μl of 0.1M NaCl, 10 mM sodium cacodylate hybridization buffer adjusted to pH 7 in order to evaluate the thermal stability of the duplex in this buffer which favors the pairings less.

EXAMPLE I

Thermal Stability of the Duplex [4'-SrU$_3$-dT$_6$-4'-SrU$_3$/P$_{11}$(SEQ ID NO: 2)]/polyrA, 4/polyrA I-I Assay of the Oligomers Concentration of 4=0.821 mM
Concentration of polyrA=4.61 mM.

I-2 Hybridization Conditions

3 μM (3.65 μl) of 4 and 3 μM (7.79 μl) of polyrA are brought into contact with 988.5 μl of the hybridization buffers (1M NaCl, 10 mM sodium cacodylate or 0.1M NaCl, 10 mM sodium cacodylate).

EXAMPLE II

Thermal Stability of Duplex 4'-SrU$_3$-dT$_6$-4'-SrU$_3$/P$_{11}$(SEQ ID NO: 2)/dC$_2$A$_{12}$C$_2$, 4/dC$_2$A$_{12}$C$_2$(SEQ ID NO: 4)

II-I Assay of the Oligomers

Concentration of 4=0.821 mM
Concentration of dC$_2$A$_{12}$C$_2$(SEQ ID NO: 4)=0.369 mM II-2 Hybridization Conditions 3 μM (3.65 μl) of 4 and 3 μM (8.11 μl) of dC$_2$A$_{12}$C$_2$(SEQ ID NO: 4) are brought into contact with 988.2 μl of the hybridization buffera (1M NaCl, 10 mM sodium cacodylate or 0.1M NaCl, 10 mM sodium cacodylate).

EXAMPLE III

Thermal Stability of the Duplex [4'-SrU$_3$-dT$_6$-4'-SrU$_3$/P$_3$PS$_5$P$_3$(SEQ ID NO: 2)]/polyrA, 5/polyrA III-1 Assay of the Oligomers Concentration of 5=0.40 mM.
Concentration of polyrA=4.61 mM.

III-2 Hybridization Conditions

3 μM (7.5 μl) of 5 and 3 μM (7.79 μl) of polyrA are brought into contact with 984.7 μl of the hybridization buffers (1M NaCl, 10 mM sodium cacodylate or 0.1M NaCl, 10 mM sodium cacodylate).

EXAMPLE IV

Thermal Stability of the Duplex
[4'-SrU$_3$-dT$_6$-4'-SrU$_3$/P$_3$PS$_5$P$_3$(SEQ ID NO: 2)]/dC$_2$A$_{12}$C$_2$(SEQ ID NO: 4), 5/polyrA

IV-I Assay of the Oligomers

Concentration of 5=0.40 mM

Concentration of $dC_2A_{12}C_2$(SEQ ID NO: 4)=0.369 mM

IV-2 Hybridization Conditions

3 µM (7.5 µl) of 5 and 3 µM (8.11 µl) of $dC_2A_{12}C_2$(SEQ ID NO: 4) are brought into contact with 984.4 µl of the hybridization buffers (1M NaCl, 10 mM sodium cacodylate or 0.1M NaCl, 10 mM sodium cacodylate).

VI. ENZYMATIC STUDIES

The recognition of nucleic acids by enzymes is for the most part of a structural nature. The replacement of the natural heteroatom of the sugar of an oligonucleotide confers on the latter a high resistance to degradation by nucleases.

The study of the hydrolysis of the β4'-thiooligoribonucleotides by these nucleases makes it possible to confirm that the replacement of the intracyclic oxygen by a sulfur atom indeed confers a higher enzymatic stability.

EXAMPLE I

Study of the enzymatic degradation of the dodecamer β(SrT)dT$_{11}$(SEQ ID NO: 3) by calf spleen phosphodiesterase. Calf spleen phosphodiesterase is an exonuclease which degrades the oligomers from their free 5' ends, thus liberating nucleotides 3' phosphate.

This study will allow us to evaluate the resistance to enzymatic degradation induced by the presence in the 5' position of a 4'-thionucleotide unit in the oligomer β(SrT)dT$_{11}$(SEQ ID NO: 3) compared to the enzymatic degradation of the oxygenated natural homolog βdT$_{12}$(SEQ ID NO: 3). The comparative stability of the two dodecamers βdT$_{12}$ (SEQ ID NO: 3) and β(SrT)dT$_{11}$(SEQ ID NO: 3) towards hydrolysis by calf spleen phosphodiesterase is presented in Table 8.

The difference in behavior between the two dodecamers is substantial; indeed, only 23% of the oligomer β(SrT)dT$_{11}$ (SEQ ID NO: 3) was hydrolyzed in 25 minutes whereas in the same period of time, the 12-mer βdT$_{12}$(SEQ ID NO: 3) was 93% degraded.

TABLE 8

Kinetics of degradation of βdT$_{12}$ (SEQ ID NO:3) and β(SrT)dT$_{11}$ (SEQ ID NO:3) by calf spleen phosphodiesterase

| Dodecamer | Degradation in 0 min | Degradation in 25 min |
|---|---|---|
| βdT$_{12}$ (SEQ ID NO:3) | 0% | 93% |
| β(SrT)dT$_{11}$ (SEQ ID NO:3) | 0% | 23% |

The variation over time of the enzymatic degradation of the two dodecamers was monitored by HPLC. We were able to plot the curve for enzymatic digestion of β(SrT)dT$_{11}$(SEQ ID NO: 3) as a function of time: $A=A_0 e^{-kt}$ (FIG. 2, A) where:

$A_0$ is the initial surface area of the 12-mer
A is the surface area of the 12-met at the instant t
t is the time
k is the first order rate constant for the degradation This curve (FIG. 2) allows us to calculate, using the EUREKA curvilinear regression software, k=0.016 min⁻¹ and the half-life period for the dodecamer $t_{1/2}=\ln 2/k=43$ min.

Figure 2:
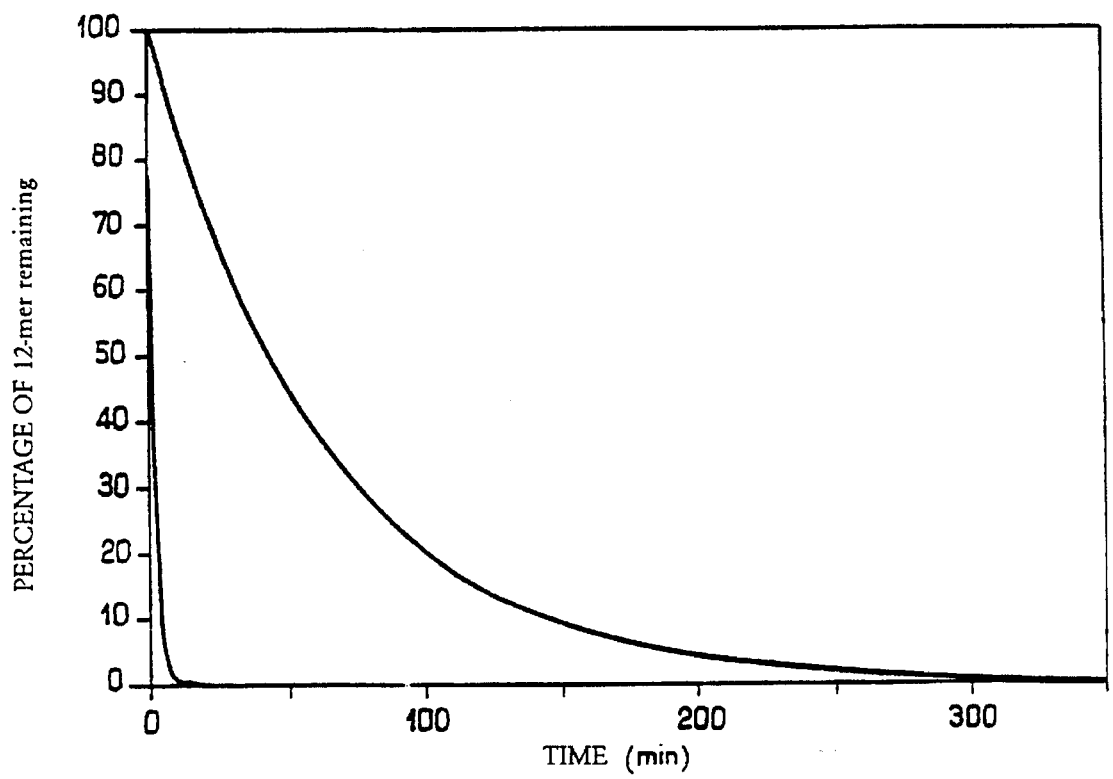
FIG. 2 represents the curve for the enzymatic digestion of beta(S$_r$T)dT$_{11}$(SEQ ID NO: 3).

Likewise, it was possible to plot the curve for enzymatic digestion of βdT$_{12}$(SEQ ID NO: 3) as a function of time, $A=A_0 e^{-kt}$ (FIG. 2). It is observed that the kinetics of degradation of βdT$_{12}$(SEQ ID NO: 3) is much more rapid than that for β(SrT)dT$_{11}$(SEQ ID NO:3); indeed, the half-life period is established at 1 minute for the natural dodecamer.

The kinetics of enzymatic degradation of the modified oligomer β(SrT)dT$_{11}$(SEQ ID NO: 3) by the 5' end has a half-life period substantially greater than that for the degradation of βSrU$_{12}$. These results show that the introduction of a thioribonucleotide unit at the 5' end of an oligomer stabilizes the latter against calf spleen phosphodiesterase.

An oligonucleotide solution (20 µl, 3 absorbance units at 260 nm) is diluted in 0.125M ammmonium acetate buffer (pH 7.0), 2.5 mM EDTA and 0.065% Tween 80 (80 µL). A commercial solution of calf spleen phosphodisesterase (2 µl, final concentration 0.008 unit/ml) is added and the mixture is incubated at 37° C. At determined times, aliquot fractions are collected (5 µl), heated at 100° C. for one minute and analyzed by HPLC.

Conditions for HPLC Analysis

The analyses were carried out on an PVDI (Polyvinylimidazole SFCC-Shandon) column protected by a precolumn and a prefilter. The elution is carried out based on a linear gradient over 20 minutes from 0.1M to 0.4M KCl in 20 mM $KH_2PO_4$ at pH 6 containing 20% acetonitrile. The flow rate was fixed at 1 ml/min and the UV detection at 260 nm.

EXAMPLE II

Study of the substrate-type activities of hexamers 4'-SrU$_6$, 4'-SrU$_6$-3'n-prOH compared with the substrate characteristics of the hexamers βrU$_6$ and αrU$_6$ in relation to various purified nucleases.

Four typical nucleases were used:

Endonuclease S1, specific for the single DNA strand hydrolyzes the phosphodiester bonds in a random manner.

Calf spleen phosphodiesterase (CSP) is a 5'-exonuclease which degrades the oligonucleotides from their 5' end and liberates nucleotides 3'-phosphates.

Snake venom phosphodiesterase (VSP) is a 3'-exonuclease-3' which liberates nucleotides 5'-phosphate after degrading the oligomer by its 3' end.

Ribobuclease A degrades an oligoribonucleotide after the pyrimidine residues.

These four enzymes were obtained from Boehringer Mannheim.

Generally, one optical density unit at 260 nm of each hexamer is brought into contact with a certain concentration of the enzyme considered and is then diluted in a sufficient quantity for 1000 µl of enzymatic digestion buffer.

Various digestion buffers were used depending on the nature of the enzyme (Table 9).

TABLE 9

Concentrations of enzyme and digestion buffers used

| Enzyme | Final concentration of enzyme (enzymatic activity units/ml) | Enzymatic digestion buffer |
|---|---|---|
| CSP | 13 × 10⁻³ | EDTA 0.025 mM pH 7 AcONH$_4$⁺ 0.125 mM |

TABLE 9-continued

Concentrations of enzyme and digestion buffers used

| Enzyme | Final concentration of enzyme (enzymatic activity units/ml) | Enzymatic digestion buffer |
|---|---|---|
| VSP | $6 \times 10^{-4}$ | Tris, HCl 0.1N pH = 9.4 MgCl$_2$ 0.01M |
| S1 | 20 | AcONa 0.05N NaCl 0.3M pH 4.7 AcZn 0.1M |
| RNAse A | $2 \times 10^{-2}$ | NaCl 300 mM Tris, HCl 10 mM pH 7.4 EDTA 5 mM |

The stock sample is divided into 10 fractions of 100 µl before being frozen at −18° C.

One aliquot fraction of 100 µl is collected and incubated in a dry oven thermostated at 37° C. for a time t and is then analyzed by analytical HPLC.

The study of the surface area of the signal corresponding to the hexamer makes it possible to measure a kinetics of degradation whose half-life period is calculated (Table 10).

TABLE 10

Enzymatic degradations

| | Half-life period (min) | | | |
|---|---|---|---|---|
| Nucleases | $\alpha rU_6$ | $\beta rU_6$ | $\beta SrU_6$ | $\beta SrU_6 3'(CH_2)_3OH$ |
| 5'-exonuclease calf spleen phosphodiesterase | * | 17 | 3900 | — |
| 3'-exonuclease snake venom | 110 | 1 | 76 | 250 |

TABLE 10-continued

Enzymatic degradations

| | Half-life period (min) | | | |
|---|---|---|---|---|
| Nucleases | $\alpha rU_6$ | $\beta rU_6$ | $\beta SrU_6$ | $\beta SrU_6 3'(CH_2)_3OH$ |
| phosphodiesterase | | | | |
| Endonuclease S1 | * | 120 | 930 | — |
| Ribonuclsaoe A | * | <1 | 670 | — |

*No degradation observed after 4 days of incubation

The hexamer 4'-SrU$_6$, 2 exhibits a high enzymatic resistance compared with that of βrU$_6$ in relation to the four nucleases (CSP, S$_1$, RNase-A and VSP).

The resistance to the 3'-exonuclease is greatly increased by introducing a propanol phosphodiester bond at the 3' end of 4'-SrU$_6$3'n-prOH, 3.

CONCLUSION

The studies showed that:

a) The homogeneous or mixed 4'-thiooligoribonucleotides bind with a good thermodynamic stability to a complementary RNA.

b) The substitution of the cyclic oxygen by a sulfur atom induces a high resistance to enzymatic degradation (cf. the comparison of the half-life period of β-rU$_6$ and β-S-rU$_6$).

All these data imply that the 4'-thiooligoribonucleotides can be considered as antisense agents in the form of homogeneous sequences or included in mixed oligomers. Furthermore, the presence of the hydroxyl functional group in 2' makes it possible to ensivage their use as artificial ribozymes, whether in the form of homogeneous or mixed sequences associated with oligonucleotides of various types, DNA or RNA, modified or otherwise at the level of the phosphate concatenation.

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
      ( A ) LENGTH: 12 bases
      ( B ) TYPE: nucleic acid
      ( C ) STRANDEDNESS: single
      ( D ) TOPOLOGY: linear ( x i ) SEQUENCE DESCRIPTION: SEQ ID NO:1:

A C A C C C A A U U    C U        1 2

( 2 ) INFORMATION FOR SEQ ID NO:2:

( i ) SEQUENCE CHARACTERISTICS:
      ( A ) LENGTH: 12 bases
      ( B ) TYPE: nucleic acid
      ( C ) STRANDEDNESS: single
      ( D ) TOPOLOGY: linear ( x i ) SEQUENCE DESCRIPTION: SEQ ID NO:2:

UUUTTTTTU UU            1 2

( 2 ) INFORMATION FOR SEQ ID NO:3:

( i ) SEQUENCE CHARACTERISTICS:
　　　　( A ) LENGTH: 12 bases
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:3:

TTTTTTTTT TT            1 2

( 2 ) INFORMATION FOR SEQ ID NO:4:

( i ) SEQUENCE CHARACTERISTICS:
　　　　( A ) LENGTH: 16 bases
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:4:

CCAAAAAAAA AAAACC       1 6

( 2 ) INFORMATION FOR SEQ ID NO:5:

( i ) SEQUENCE CHARACTERISTICS:
　　　　( A ) LENGTH: 12 bases
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:5:

UUUUUUUUU UU            1 2

What is claimed is:

1. An oligomeric compound comprising a first oligothionucleotide, wherein said oligothionucleotide is an oligo-4'-thio-2'-deoxyribonucleotide which comprises 4'-thio-2'-deoxyribonucleotides linked by internucleotide linkages, or an oligo-4'-thioribonucleotide which comprises 4'-thioribonucleotides linked by internucleotide linkages.

2. The oligomeric compound of claim 1, having the formula:

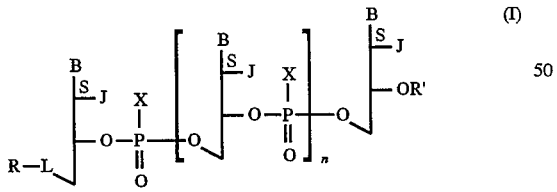

wherein:
the B radicals are, independently, nucleic acid bases and are attached to the glycoside ring according to a non-natural alpha anomeric configuration;
the X radicals are, independently, an oxoanion O⁻, a thioanion S⁻, an alkyl group, an alkoxy group, a thioalkyl group, an alkyl substituted by a nitrogen-containing heterocycle, an alkoxy radical substituted by a nitrogen-containing heterocycle, or a —Y—Z group;
R and R' are, independently, a hydrogen atom, a —Y—Z group, a Y'—Z' group, an RNA type oligonucleotide, or a DNA type oligonucleotide;

Y and Y' are, independently, a straight or branched alkylene radical —alk—, or a radical selected from the group consisting of

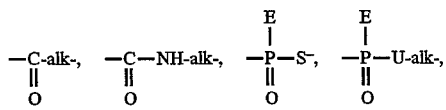

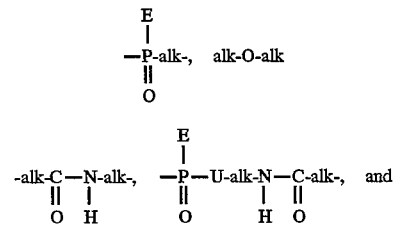

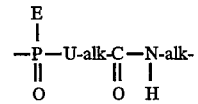

wherein:
U is O, S, or N;
E is an oxoanion O⁻, a thioanion S⁻, an alkyl group, an alkoxy group, a thioalkyl group, an alkyl substituted by a nitrogen-containing heterocycle, or an alkoxy radical substituted by a nitrogen-containing heterocycle;
J is a hydrogen atom or a hydroxyl group;

Z and Z' are, independently, a hydroxyl group or an effector selected from the group consisting of polycyclic compounds having a planar configuration, acridine, proflavine, biotin, furocoumarin, daunomycin, anthracycline, ethylenediaminetetraacetic acid, diethylenetriaminepentaacetic acid, porphyrins, 1,10-phenanthroline, phenanthridine, ellipticine, ellipticinium, dipyrido(1,2-a:3',2'-d)imidazole, diazapyrene, 4-azidoacetophenone, ethylene-imine, beta-chloroethylamine, psoralen, methylpyrroporphyrin, and aromatic compounds absorbing near-ultraviolet or visible radiations;

n is an integer including 0;

L is an oxygen atom, a sulfur atom, or an —NH— group.

3. The oligomeric compound of claim 2, wherein Y and Y' are independently

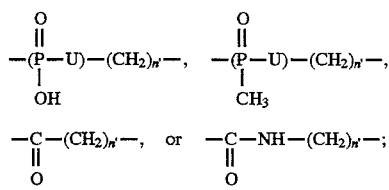

wherein U is O, S, or N, and n' is an integer from 1 to 10.

4. The oligomeric compound of claim 2, wherein L is oxygen, R and R' are hydrogen atoms, and B is a natural nucleic acid base.

5. The oligomeric compound of claim 2, wherein Z and Z' are independently acridine, furocoumarin, daunomycin, 1,10-phenanthroline, phenanthridine, proflavine, porphyrins, dipyrido(1,2-a:3'-d) imidazole, ellipticine, ellipticinium, or diazapyrene.

6. The oligomeric compound of claim 2, wherein the nucleic acid bases are thymine, adenine, 2-aminoadenine, cytosine, guanine, uracil, 5-bromouracil, 8-azidoadenine, 7-deazaadenine, 7-deazaguanine, 4-azidocytosine, or 4-azidothymine.

7. The oligomeric compound of claim 2, wherein J is OH.

8. The oligomeric compound of claim 1 further comprising an RNA type oligonucleotide or a DNA type oligonucleotide linked by an internucleotide linkage to said compound of claim 1, wherein oxygen is the heteroatom of the furanose ring of the nucleotides of said DNA type oligonucleotide or RNA type oligonucleotide.

9. The oligomeric compound of claim 1 further comprising an RNA type oligonucleotide or a DNA type oligonucleotide linked by internucleotide linkages at one or each of its ends to said compound of claim 1, wherein oxygen is the heteroatom of the furanose ring of the nucleotides of said DNA type oligonucleotide or RNA type oligonucleotide.

10. The oligomeric compound of claim 2 further comprising an RNA type oligonucleotide or a DNA type oligonucleotide linked by an internucleotide linkage to said compound of claim 2, wherein oxygen is the heteroatom of the furanose ring of the nucleotides of said DNA type oligonucleotide or RNA type oligonucleotide.

11. The oligomeric compound of claim 2 further comprising an RNA type oligonucleotide or a DNA type oligonucleotide linked by internucleotide linkages at one or each of its ends to said compound of claim 2, wherein oxygen is the heteroatom of the furanose ring of the nucleotides of said DNA type oligonucleotide or RNA type oligonucleotide.

12. The oligomeric compound of claim 8, further comprising a second oligothionucleotide linked to said DNA type oligonucleotide, wherein said second oligothionucleotide comprises 4'-thio-2'-deoxyribonucleotides or 4'-thioribonucleotides linked by internucleotide linkages.

13. The oligomeric compound of claim 10, further comprising a second oligothionucleotide linked to said DNA type oligonucleotide, wherein said second oligothionucleotide comprises 4'-thio-2'-deoxyribonucleotides or 4'-thioribonucleotides linked by internucleotide linkages.

14. The oligomeric compound of claim 12, wherein said first and second oligothionucleotides are oligo-4'-thioribonucleotides.

15. The oligomeric compound of claim 13, wherein said first and second oligothionucleotides are oligo-4'-thioribonucleotides.

16. A process for preparing the oligomeric compound of claim 1, comprising the steps:

(a) synthesizing an oligothionucleotide using 4'-thionucleotides, wherein the internucleotide linkages of said oligothionucleotide are selected from the group consisting of phosphodiester, phosphotriester, phosphoramidite, and hydrogen phosphonate, and wherein said 4'-thionucleotides are completely protected; and (b) removing the protecting groups to obtain said oligomeric compound.

17. A process for preparing the oligomeric compound of claim 2, wherein both Z and Z' are OH, by a phosphoramidite method comprising the steps:

(a) protecting the 5' position of a 4'-thionucleotide or an oligo-4'-thionucleotide with dimethoxytrityl and protecting the 3'position of a 4'-thionucleotide or an oligo-4'-thionucleotide with methyl diisopropylaminophosphoramidite;

(b) functionalizing a solid support having an amino group by incorporating a 4'-thionucleoside derivative having a succinyl linkage between the 3'-hydroxyl group of the 4'-thionucleoside derivative and the amino group of the solid support;

(c) elongating the oligothionucleotide chain in a synthesizing reactor; and (d) detaching the oligothionucleotide from the solid support, deprotecting the 5' and 3' positions, and purifying said oligomeric compound.

18. The oligomeric compound of claim 1 further comprising a linked effector, which is an intercalating agent or a chemical or photoactivable radical, wherein said effector is a polycyclic compound having a planar configuration, ethylenediaminetetraacetic acid, diethylenetriaminepentaacetic acid, porphyrins, 1,10-phenanthroline, 4-azidoacetophenone, ethylene-imine, beta-chloroethylamine, psoralen, acridine, proflavine, biotin, furocoumarin, daunomycin, anthracycline, phenanthridine, ellipticine, ellipticinium, methylpyrroporphyrin, dipyrido(1,2-a:3',2'-d) imidazole, diazapyrene, or an aromatic compound absorbing near-ultraviolet or visible radiations.

* * * * *